(12) United States Patent
Goredema et al.

(10) Patent No.: US 7,560,587 B2
(45) Date of Patent: *Jul. 14, 2009

(54) BIS[UREA-URETHANE] COMPOUNDS

(75) Inventors: Adela Goredema, Mississauga (CA);
Rina Carlini, Mississauga (CA);
Christine E. Bedford, Oakville (CA);
Marcel P. Breton, Mississauga (CA);
Eniko Toma, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 738 days.

This patent is subject to a terminal disclaimer.

(21) Appl. No.: 11/004,331

(22) Filed: Dec. 4, 2004

(65) Prior Publication Data

US 2006/0122427 A1    Jun. 8, 2006

(51) Int. Cl.
*C07C 275/14*    (2006.01)

(52) U.S. Cl. ................. 560/158; 106/31.29; 106/31.43; 106/31.61; 106/31.75

(58) Field of Classification Search ................. 560/158; 106/31.29, 31.43, 31.61, 31.75
See application file for complete search history.

(56) References Cited

U.S. PATENT DOCUMENTS

| | | | |
|---|---|---|---|
| 2,703,808 A | 3/1955 | Buckman | 260/456 |
| 3,653,932 A | 4/1972 | Berry et al. | 106/22 |
| 4,314,924 A | 2/1982 | Haubennestel et al. | |
| 4,384,102 A | 5/1983 | Rasshofer et al. | 528/73 |
| 4,390,369 A | 6/1983 | Merritt et al. | 106/31 |
| 4,484,948 A | 11/1984 | Merritt et al. | 106/31 |
| 4,566,981 A | 1/1986 | Howells | 252/8.8 |
| 4,684,956 A | 8/1987 | Ball | 346/1.1 |
| 4,790,961 A | 12/1988 | Weiss et al. | 260/376 |
| 4,851,045 A | 7/1989 | Taniguchi | 106/31 |
| 4,889,560 A | 12/1989 | Jaeger et al. | 106/27 |
| 4,889,761 A | 12/1989 | Titterington et al. | 428/195 |
| 5,006,170 A | 4/1991 | Schwarz et al. | 106/20 |
| 5,151,120 A | 9/1992 | You et al. | 106/27 |
| 5,221,335 A | 6/1993 | Williams et al. | 106/23 A |
| 5,298,618 A | 3/1994 | Speranza et al. | 540/454 |
| 5,372,852 A | 12/1994 | Titterington et al. | 427/288 |
| 5,496,879 A | 3/1996 | Griebel et al. | 524/320 |
| 5,621,022 A | 4/1997 | Jaeger et al. | 523/161 |
| 5,892,116 A | 4/1999 | Weiss et al. | 564/281 |
| 6,320,018 B1 | 11/2001 | Sijbesma et al. | 528/310 |
| 6,420,466 B1 | 7/2002 | Haubennestel et al. | 524/195 |
| 6,471,758 B1 | 10/2002 | Kelderman et al. | 106/31.29 |
| 6,548,476 B1 | 4/2003 | Wu et al. | 514/2 |
| 6,761,758 B2 | 7/2004 | Boils-Boissier et al. | 106/31.29 |
| 2001/0044553 A1 | 11/2001 | Kabashima et al. | 560/157 |
| 2003/0079644 A1 | 5/2003 | Smith et al. | 106/31.29 |
| 2003/0105185 A1 | 6/2003 | Goodbrand et al. | 523/160 |
| 2004/0060474 A1 | 4/2004 | Boils-Boissier et al. | 106/31.29 |
| 2004/0065227 A1 | 4/2004 | Breton et al. | 106/31.29 |
| 2004/0075723 A1 | 4/2004 | Breton et al. | 347/99 |
| 2004/0158063 A1 | 8/2004 | Boils-Boissier et al. | 544/180 |

FOREIGN PATENT DOCUMENTS

| | | |
|---|---|---|
| EP | 0 056 153 | 12/1985 |
| EP | 0 187 352 B1 | 7/1986 |
| EP | 0 206 286 A1 | 12/1986 |
| EP | 0 160 402 | 7/1991 |
| EP | 1 067 157 B1 | 1/2001 |
| EP | 1 350 507 A1 | 10/2003 |
| EP | 1 422 073 A1 | 5/2004 |
| WO | WO/9011283 | 10/1990 |
| WO | WO 94/04619 | 3/1994 |
| WO | WO 97/24364 | 7/1997 |
| WO | WO 00/55149 | 9/2000 |
| WO | WO 03/040135 | 5/2003 |
| WO | WO 03/084508 | 10/2003 |
| WO | WO 2005/047231 A | 5/2005 |

OTHER PUBLICATIONS

U.S. Appl. No. 11/004,682, filed Dec. 4, 2004, entitled "*Trans*-1,2-cyclohexane bis[urea-urethane] Compounds," by Adela Goredema et al.
U.S. Appl. No. 11/004,332, filed Dec. 4, 2004, entitled "Phase Change Inks Containing *Trans*-1,2-cyclohexane bis[urea-urethane] Compounds," by Adela Goredema et al.
U.S. Appl. No. 11/004,333, filed concurrently herewith, entitled "Phase Change Inks Containing Bis[urea-urethane] Compounds," by Adela Goredema et al.
U.S. Appl. No. 60/633,331, filed Dec. 4, 2004, entitled "Processes for Preparing Bis [urea-urethane] Compounds," by Adela Goredema.
Copending U.S. Appl. No. 11/004,761, filed Dec. 4, 2004, entitled "Curable *Trans*-1,2-cyclohexane bis[urea-urethane] Compounds," by Rina Carlini et al.

(Continued)

*Primary Examiner*—Peter G O'Sullivan
(74) *Attorney, Agent, or Firm*—Oliff & Berridge, PLC

(57) ABSTRACT

Disclosed is a bis(urea-urethane) compound of the formula $$R_1-O-\underset{\|}{\overset{O}{C}}-NH-R_2-NH-\underset{\|}{\overset{O}{C}}-\underset{R_4}{\overset{|}{N}}-R_3-\underset{R_5}{\overset{|}{N}}-\underset{\|}{\overset{O}{C}}-NH-$$

$$-R_2'-NH-\underset{\|}{\overset{O}{C}}-O-R_1'$$

wherein $R_1$ and $R_1'$ each, independently of the other, is an alkyl group, wherein at least one of $R_1$ and $R_1'$ has at least about 6 carbon atoms, $R_2$ and $R_2'$ each, independently of the other, is an alkylene group, wherein at least one of $R_2$ and $R_2'$ has at least about 3 carbon atoms, $R_3$ is an alkylene group having at least about 2 carbon atoms, and $R_4$ and $R_5$ each, independently of the other, is a hydrogen atom or an alkyl group, and wherein $R_1$ and $R_1'$ each contain no more than 2 fully fluorinated carbon atoms.

54 Claims, No Drawings

OTHER PUBLICATIONS

Copending U.S. Appl. No. 11/004,451, filed Dec. 4, 2004, entitled "Phase Change Inks Containing Curable *Trans*-1,2-cyclohexane bis[urea-urethane] Compounds," by Rina Carlini, et al.
Copending U.S. Appl. No. 10/794,930, filed Mar. 5, 2004, entitled "Guanidinopyrimidinone Compounds and Phase Change Inks Containing Same," by Danielle C. Boils-Boissier, et al.
Copending U.S. Appl. No. 10/810,370, filed Mar. 26, 2004, entitled "Alkylated Urea and Triaminotriazine Compounds and Phase Change Inks Containing Same," by Marcel P. Breton, et al.
English abstract for DE 4205636AL.
English abstract for DE 4205713AL.
"Cyclic Bis-Urea Compounds as Gelators for Organic Solvents," J. van Esch et al., *Chem. Eur. J.* 1999, 5, No. 3, pp. 937-950.
"The Design of Organic Gelators Based on a Family of Bis-Ureas," R. E. Meléndez et al., *Mat. Res. Soc. Symp. Proc.* 2000, 604, pp. 335-340.
"Formation of Organogels by Intermolecular Hydrogen Bonding Between Ureylene Segment," K. Hanabusa et al., *Chem. Lett.* 1996 pp. 885-886.
"Low Molecular Weight Gelators for Organic Solvents," J. van Esch et al., in *Supramolecular Science: Where Is It and Where It Is Going*, R. Ungaro and E. Dalcanale, Eds., 1999, Netherlands: Kluwer Academic Publishers, pp. 233-259.
"Organogels and Low Molecular Mass Organic Gelators," D. J. Abdallah and R. G. Weiss, *Adv. Mater.* 2000, 12, No. 17, Sep. 1, pp. 1237-1247.
"Remarkable Stabilization of Self-Assembled Organogels by Polymerization," M. de Loos et al., *J. Am. Chem. Soc.* 1997, 119, 12675-12676.
"Low-molecular weight organogelators," P. Terech, in *Specialist Surfactants*, I.D. Robb, Ed., 1997, London: Chapman & Hall, pp. 208-268.
"New Functional Materials Based on Self-Assembling Organogels: From Serendipity Towards Design," J. H. van Esch and B. L. Feringa, *Angew. Chem. Int. Ed.* 2000, 39, No. 13, pp. 2263-2266.
"Synthesis and Self-Assembling Properties of Polymerizable Organogelators," G. Wang and A. D. Hamilton, *Chem. Eur. J.* 2002, 8, No. 8, pp. 1954-1961.
"Low Molecular Mass Gelators of Organic Liquids and the Properties of their Gels," P. Terech and R.G. Weiss, *Chem, Rev.* 1997, 97, pp. 3133-3159.
"Towards a Phenomenological Definition of the Term 'Gel'," K. Amdal et al., *Polymer Gels and Networks*, 1993, 1, pp. 5-17.
English abstract for PCT Patent Publication WO 00/55149.
English abstract for EP 1 048 681.
English abstract for JP 10310633.
English Abstract for JP 59030919.
"Reversible Polymers Formed from Self-Complementary Monomers Using Quadruple Hydrogen Bonding," R. P. Sijbesma et al., *Science*, vol. 278, p. 1601 (1997).
"Supramolecular Polymers," R. Dagani, *Chemical and Engineering News*, p. 4 (Dec. 1997).
"Supramolecular Polymers from Linear Telechelic Siloxanes with Quadruple-Hydrogen-Bonded Units," J.H.K. Hirschberg et al., *Macromolecules*, vol. 32, p. 2696 (1999).
"Design and Synthesis of 'Smart' Supramolecular Liquid Crystalline Polymers via Hydrogen-Bond Associations," A.C. Griffin et al., *PMSE Proceedings*, vol. 72, p. 172 (1995).
"The Design of Organic Gelators: Solution and Solid State Properties of a Family of Bis-Ureas," Andrew J. Carr et al., *Tetrahedron Letters*, vol. 39, p. 7447 (1998).
"Hydrogen-Bonded Supramolecular Polymer Networks," Ronald F.M. Lange et al., *Journal of Polymer Science, Part A: Polymer Chemistry*, vol. 37, p. 3657 (1999).
"Combining Self-Assembly and Self-Association—Towards Columnar Supramolecular Structures in Solution and in Liquid-Crystalline Mesophase," Arno Kraft et al., *Polym. Mater. Sci. Eng.*, vol. 80, p. 18 (1999).
"Facile Synthesis of β-Keto Esters from Methyl Acetoacetate and Acid Chloride: The Barium Oxide/Methanol System," Y. Yuasa et al., *Organic Process Research and Development*, vol. 2, p. 412 (1998).

"Self-Complementary Hydrogen Bonding of 1,1'-Bicyclohexylidene-4,4'-dione Dioxime. Formation of a Non-Covalent Polymer," F. Hoogesteger et al., *Tetrahedron*, vol. 52, No. 5, p. 1773 (1996).
Molecular Tectonics. Three-Dimensional Organic Networks with Zeolite Properties, X. Wang et al., *J. Am. Chem. Soc.*, vol. 116, p. 12119 (1994).
"Helical Self-Assembled Polymers from Cooperative Stacking of Hydrogen-Bonded Pairs," J. H. K. Ky Hirschberg et al., *Nature*, vol. 407, p. 167 (2000).
"New Supramolecular Arrays based on Interactions between Carboxylate and Urea Groups: Solid-State and Solution Behavior," Abdullah Zafar et al., *New J. Chem.*, 1998, 137-141.
"The Unusual Molecular Organization of 2,3-Bis(n-hexyloxy)-anthracene in the Crystal. A Hint to the Origin of the Gelifying Properties of 2,3-Bis(n-alkyloxy)anthracenes?", J-L. Pozzo et al., *J. Chem. Soc., Perkin Trans.*, 2, 824-826 (2001).
"The Quest for the Simplest Possible Organogelators and Some Properties of their Organogels," D. Abdallah et al., *J. Braz. Chem. Soc.*, vol. 11, No. 3, 209-218 (2000).
"Organogel Electrolytes Based on a Low Molecular Weight Gelator: 2,3-Bis(n-decyloxy)anthracene," F. Placin et al., *Chem. Mater. 13*, 117-121 (2001).
"Novel Vesicular Aggregates of Crown-Appended Cholesterol Derivatives Which Act as Gelators of Organic Solvents and as Templates for Silica Transcription," J. Jung et al., *J. Am. Chem. Soc,*, vol. 122, No. 36, 8648-8653 (2000).
"n-Alkanes Gel n-Alkanes (and Many Other Organic Liquids)," D. Abdallah et al., *Langmuir*, 16, 352-355 (2000).
"Low Molecular Mass Gelators of Organic Liquids and the Properties of their Gels," P. Terech et al., *Chem. Rev.*, 97, 3133-3159 (1997).
"Organogels and Low Molecular Mass Organic Gelators," D. Abdallah et al., *Adv. Mater.*, 12, No. 17, 1237 (2000).
"Making it All Stick Together: the Gelation of Organic Liquids by Small Organic Molecules," F. Schoonbeek, Doctoral Thesis, U. of Groningen, Netherlands, Apr. 2001; Twieg et al., *Macromolecules*, vol. 18, p. 1361 (1985).
"Synthesis and Reactions of Polyhydric Alcohols I. Synthesis and Reactions of p-Toluenesulfonates of Polyhydric Alcohols," *Zhurnal Obshchei Khimii*, vol. 35, No. 5, p. 804-807 (1965).
"The Chemotherapy of Schistosomiasis. Part I. Derivatives and Analogs of αω-Di-(p-aminophenoxy)alkanes," J. Ashley et al., *J. Chem. Soc.* 1958, 3293.
"Remarkably Simple Small Organogelators: Di-n-alkoxy-benzene Derivatives," G. Clavier et al., *Tetrahedron Letters*, 40, 9021-9024 (1999).
"Rational Design of Low Molecular Mass Organogelators: Toward a Library of Functional N-Acyl-1-ω-Amino Acid Derivatives," G. Mieden-Gundert et al., *Angew. Chem. Int. Ed.*, 40, No. 17, 3164-3166 (2001).
"Rational Design of New Acid-Sensitive Organogelators," J-L. Pozzo et al., *J. Mater. Chem.*, vol. 8, pp. 2575-2577 (1998).
J. T. Thurston et al., *J. Am. Chem. Soc.*, vol. 73, pp. 2981-3008 (1951). *J. Am. Chem. Soc.*, vol. 96, pp. 1082-1087 (1974).
J-L. Pozzo et al., "Different Synthetic routes towards Efficient Organogelators: 2,3-Substituted Anthracenes," *Tetrahedron*, vol. 53, No. 18, pp. 6377-6390 (1997).
J-L. Pozzo et al., "Photochromic Guests in Organogels," *Mol. Cryst. Liq. Cryst.*, vol. 344, pp. 101-106 (2000).
Y.C. Lin, R.G. Weiss, *Macromolecules*, vol. 20, p. 414 (1987).
L. Lu et al., "New Lyotropic Phases (Thermally-Reversible Organogels) of Simple Tertiary Amines and Related Tertiary and Quarternary Ammonium Halide Salts," *Chem. Commun.*, 1996, p. 2029.
A. Ikeda et al., *Rep. Asahi Glass Found. Ind. Technol.*, vol. 61, p. 115, (1992).
Rabolt et al., *Macromolecules*, vol. 17, p. 2786 (1984).
D.J. Abdallah et al., *Chem. Mater.*, vol. 11, p. 2907 (1999).
Ralston et al., *J. Org. Chem.*, vol. 9, p. 259 (1944).
L. Lu et al., "New Lyotropic Phases (Thermally-Reversible Organogels) of Simple Tertiary Amines Related Tertiary and Quarternary Ammonium Halide Salts," *Chem. Commun.*, 1996, p. 2029.

*J. Prakt. Chem.*, vol. 327 (3), pp. 383-398 (1985).

B.L. Feringa et al., *J. Org. Chem.*, vol. 53, p. 1125 (1988).

J.C. DeJong et al., *Tetrahedron Lett.*, vol. 30, p. 7239 (1989).

J.C. DeJong, Ph.D. thesis, University of Groningen, The Netherlands, 1991.

F. A. Neugebauer et al., *Chem. Ber.*, 1976, 109, 2389.

U. Zehavi et al., *J. Org. Chem.*, vol. 26, pp. 1097-1101 (1961).

J. March, *Advanced Organic Chemistry*, 4th Edition, pp. 903 and 1091-1092, Wiley Interscience (New York 1992).

J. Crossley Maxwell, "The Synthesis of Some Lipophilic Tetradentate Ligands for Use in the Formation of Metal-Linked Polymers," *Aust. J. Chem.*, vol. 47, pp. 723-738 (1994).

V.J. Wotring et al., *Analytical Chemistry*, vol. 62, No. 14, pp. 1506-1510 (1990).

Tabushi et al., *J. Am. Chem. Soc.*, vol. 103, pp. 6152-6157 (1981).

T. Giorgi et al., "Gel-like lyomesophases formed in organic solvents by self-assembled guanine ribbons," *Chemistry—A European Journal* (2002), 8(9), 2143-2152.

T. Suyamaet al., "A method for the preparation of substituted biguanides," *Nippon Kagaku Kaishi* (1989), (5), 884-7.

English abstract for Polish Patent Publication PL 148060 B1.

English abstract for Polish Patent Publication PL 134682 B1.

C.S. Snijder et al., *Chem. Eur. J.*, vol. 1, No. 9, pp. 594-597 (1995).

S. Senda et al., Gifu Coll. Pharm., Gifu, Japan. *Yakugaku Zasshi* (1969), 89 (2), 254-259.

B. Gluncic et al, *Acta Pharm. Jugosl.* (1986), 36(4), 393-404.

English abstract for Canadian Patent Publication CA 941377.

M. Klein, Recent Dev. Mass Spectrom. Biochem. Med., [Proc. Int. Symp.], 4th (1978), Meeting Date 1977, 1, 471-82.

English abstract for Japanese Patent Publication JP 62181279.

T. Wada et al., "A New Boranophosphorylation Reaction for the Synthesis of Deoxyribonucleoside Boranophosphates," *Tetrahedron Letters*, vol. 43, No. 23, pp. 4137-4140 (2002).

R. Schirrmacher et al., "Dimethylpyridin-4-ylamine-catalysed alcoholysis of 2-amino-N,N,N-trimethyl-9H-purine-6-ylammonium chloride: An effective route to O6-substituted guanine derivatives from alcohols with poor nucleophilicity," *Synthesis*, vol. 4, pp. 538-542 (2002).

Z. Situ, "Synthesis of Tricyclic Derivatives of Guanine Analogue Catalyzed by $KF-Al_2O_3$," *Huaxue Shiji*, vol. 24, No. 1, p. 57 (2002).

English abstract for Korean Patent 2000003081 (Korean Patent Application KR 1998-24185).

S. Bailey et al., "Synthesis and Antiviral Activity of 9-Alkoxypurines: New 9-(Hydroxyalkoxy) Derivatives of Guanine and 8-Methylguanine," *Antiviral Chem. Chemother.*, vol. 5, No. 1, pp. 21-33 (1994).

English abstract for Japanese Patent Publication JP 06157529.

M. R. Harnden et al., "Synthesis, Oral Bioavailability and In Vivo Activity of Acetal Derivatives of the Selective Antiherpesvirus Agent 9-(3-Hydroxypropoxy)Guanine (BRL44385)," *Antiviral Chem. Chemother.*, vol. 5, No. 3, pp. 147-154 (1994).

Spanish Patent Publication ES 2047457.

B. K. Bhattacharaya et al., "Synthesis of Certain N- and C-alkyl Purine Analogs," *J. Heterocycl. Chem.*, vol. 30, No. 5, pp. 1341-1349 (1993).

English abstract for Polish Patent Publication PL 148969.

Van Esch J et al., "Di-urea Compounds as Gelators for Organic Solvents", Tetrahedron Letters, Elsevier, Amsterdam, NL, vol. 38, No. 2, Jan. 13, 1997, pp. 281-284.

Versteegen, Ron M et al., "Synthesis and Characterization of Segmented Copoly(ether urea)s With Uniform Hard Segments", Macromolecules, 38(8), 3176-3184 CODEN: Mamobx: ISSN: 0024-9297, Mar. 24, 2005, p. 3180.

Carr A J et al., "The Design of Organic Gelators: Solution and Solid State Properties of a Family of Bis-Ureas", Tetrahedron Letters, Elsevier, Amsterdam N, vol. 39, No. 41, ISSN: 0040-4039, Oct. 8, 1988, pp. 7447-7450.

BIS[UREA-URETHANE] COMPOUNDS

CROSS-REFERENCE TO RELATED APPLICATIONS

Copending Application U.S. Ser. No. 11/004,682, filed concurrently herewith, entitled "Trans-1,2-cyclohexane bis[urea-urethane] Compounds," with the named inventors Adela Goredema, Rina Carlini, Marcel P. Breton, Jeffery H. Banning, and Eniko Toma, the disclosure of which is totally incorporated herein by reference, discloses trans-1,2-cyclohexane bis[urea-urethane] compounds of the formulae

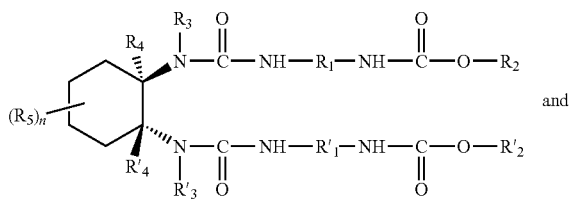

and

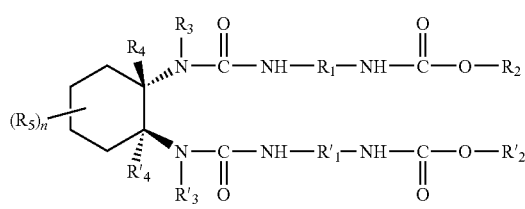

wherein $R_1$ and $R'_1$ each, independently of the other, is an alkylene group, an arylene group, an arylalkylene group, or an alkylarylene group, $R_2$ and $R'_2$ each, independently of the other, is an alkyl group, an aryl group, an arylalkyl group, or an alkylaryl group, $R_3$ and $R'_3$ each, independently of the other, is a hydrogen atom or an alkyl group, $R_4$ and $R'_4$ each, independently of the other, is a hydrogen atom, a fluorine atom, an alkyl group, or a phenyl group, n is an integer of 0, 1, 2, 3, or 4, and $R_5$ is an alkyl group, an aryl group, an arylalkyl group, an alkylaryl group, or a substituent other than an alkyl, aryl, arylalkyl, or alkylaryl group.

Copending Application U.S. Ser. No. 11/004,332, filed concurrently herewith, entitled "Phase Change Inks Containing Trans-1,2-cyclohexane bis[urea-urethane] Compounds" with the named inventors Adela Goredema, Rina Carlini, Marcel P. Breton, and Jeffery H. Banning, the disclosure of which is totally incorporated herein by reference, discloses phase change inks comprising a phase change ink carrier and a trans-1,2-cyclohexane bis[urea-urethane] compound of the formula

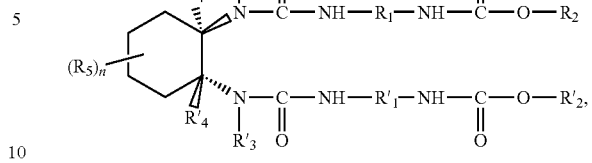

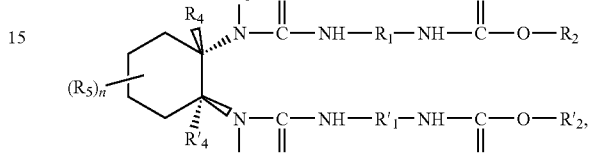

or mixtures thereof, wherein $R_1$ and $R'_1$ each, independently of the other, is an alkylene group, an arylene group, an arylalkylene group, or an alkylarylene group, $R_2$ and $R'_2$ each, independently of the other, is an alkyl group, an aryl group, an arylalkyl group, or an alkylaryl group, $R_3$ and $R'_3$ each, independently of the other, is a hydrogen atom or an alkyl group, $R_4$ and $R'_4$ each, independently of the other, is a hydrogen atom, a fluorine atom, an alkyl group, or a phenyl group, n is an integer of 0, 1, 2, 3, or 4, and $R_5$ is an alkyl group, an aryl group, an arylalkyl group, an alkylaryl group, or a substituent other than an alkyl, aryl, arylalkyl, or alkylaryl group.

Copending Application U.S. Ser. No. 11/004,333, filed concurrently herewith, entitled "Phase Change Inks Containing Bis[urea-urethane] Compounds," with the named inventors Adela Goredema, Rina Carlini, Christine E. Bedford, and Marcel P. Breton, the disclosure of which is totally incorporated herein by reference, discloses a phase change ink composition comprising a phase change ink carrier and a bis[urea-urethane] compound of the formula

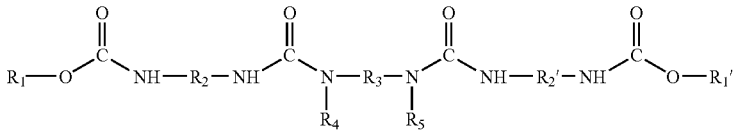

wherein $R_1$ and $R_1'$ each, independently of the other, is an alkyl group, an aryl group, an arylalkyl group, or an alkylaryl group, $R_2$ and $R_2'$ each, independently of the other, is an alkylene group, an arylene group, an arylalkylene group, or an alkylarylene group, $R_3$ is an alkylene group, an arylene group, an arylalkylene group, or an alkylarylene group, and $R_4$ and $R_5$ each, independently of the other, is a hydrogen atom or an alkyl group.

Copending Application U.S. Ser. No. 60/633,331, filed concurrently herewith, entitled "Processes for Preparing Bis [urea-urethane] Compounds," with the named inventor Adela Goredema, the disclosure of which is totally incorporated herein by reference, discloses a process for preparing bis [urea-urethane] compounds of the formula

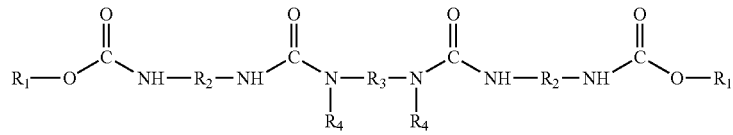

wherein $R_1$ is an alkyl group, an aryl group, an arylalkyl group, or an alkylaryl group, $R_2$ is an alkylene group, an arylene group, an arylalkylene group, or an alkylarylene group, $R_3$ is an alkylene group, an arylene group, an arylalkylene group, or an alkylarylene group, and $R_4$ is a hydrogen atom or an alkyl group, said process comprising: (1) first adding a monoalcohol reactant of the formula $R_1$—OH to a diisocyanate reactant of the formula OCN—$R_2$—NCO, said monoalcohol being added in an amount of from about 0.8 mole of monoalcohol per every one mole of diisocyanate to about 1.2 moles of monoalcohol per every one mole of diisocyanate, said monoalcohol and said diisocyanate reactants being admixed in a solvent, said reactants and said solvent being present in a relative amount of at least about 10 milliliters of solvent per every 1 millimole of diisocyanate, said addition of monoalcohol occuring while heating the diisocyanate and the solvent to a temperature of from about 25° C. to about 125° C.; (2) subsequent to addition of the monoalcohol, maintaining the temperature of the reaction mixture thus formed at a temperature of from about 25° C. to about 125° C. until the reaction between the monoalcohol and the diisocyanate is complete; and (3) subsequent to step (2), adding to the reaction mixture a diamine of the formula

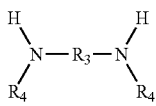

without isolating the reaction product of step (2), thereby forming a compound of the formula

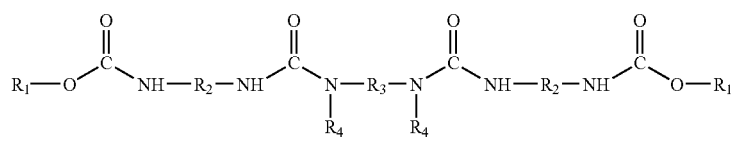

in desirably high yield.

Copending Application U.S. Ser. No. 11/004,761, filed concurrently herewith, entitled "Curable Trans-1,2-cyclohexane bis[urea-urethane] Compounds," with the named inventors Rina Carlini, Eniko Toma, Peter G. Odell, and Jeffery H. Banning, the disclosure of which is totally incorporated herein by reference, discloses Curable trans-1,2-cyclohexane bis[urea-urethane] compounds of the formulae

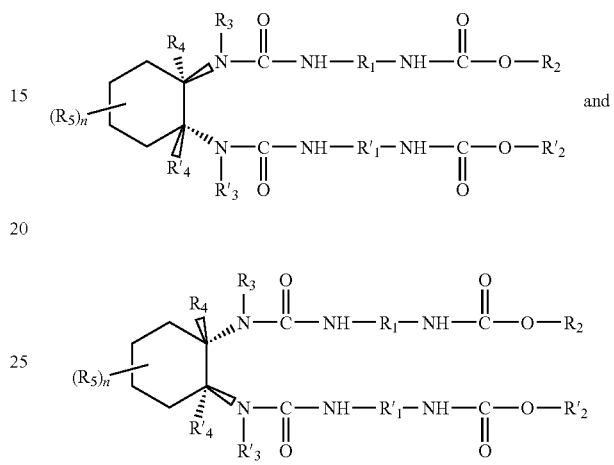

wherein $R_1$ and $R'_1$ each, independently of the other, are alkylene, arylene, arylalkylene, or alkylarylene groups, $R_2$ and $R'_2$ each, independently of the other, are alkyl, aryl, arylalkyl, or alkylaryl groups, $R_3$ and $R'_3$ each, independently of the other, are hydrogen atoms or alkyl groups, $R_4$ and $R'_4$ each, independently of the other, are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending Application U.S. Ser. No. 11/004,451, filed concurrently herewith, entitled "Phase Change Inks Containing Curable Trans-1,2-cyclohexane bis[urea-urethane] Compounds," with the named inventors Rina Carlini, Eniko Toma, Peter G. Odell, and Jeffery H. Banning, the disclosure of which is totally incorporated herein by reference, discloses phase change inks comprising a phase change ink carrier and one or more curable trans-1,2-cyclohexane bis[urea-urethane] compounds of the formulae

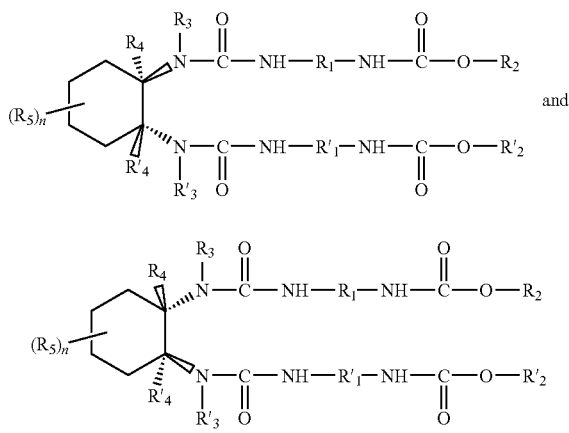

wherein $R_1$ and $R'_1$ are alkylene, arylene, arylalkylene, or alkylarylene groups, $R_2$ and $R'_2$ are alkyl, aryl, arylalkyl, or alkylaryl groups, $R_3$ and $R'_3$ are hydrogen atoms or alkyl groups, $R_4$ and $R'_4$ are hydrogen atoms, fluorine atoms, alkyl groups, or phenyl groups, n is an integer of 0, 1, 2, 3, or 4, and $R_5$ is an alkyl, aryl, arylalkyl, or alkylaryl group, or a substituent other than an alkyl, aryl, arylalkyl, or alkylaryl group, provided that at least one of $R_1$, $R'_1$, $R_2$, $R'_2$, $R_3$, $R'_3$, $R_4$, $R'_4$, or one or more of $R_5$ is an alkyl, alkylene, arylalkyl, arylalkylene, alkylaryl, or alkylarylene group containing an ethylenic unsaturation rendering the compound curable upon exposure to heat and/or actinic radiation.

Copending Application U.S. Ser. No. 09/949,315, filed Sep. 7, 2001, U.S. Publication 20030079644, entitled "Aqueous Ink Compositions," with the named inventors Thomas W. Smith, David J. Luca, and Kathleen M. McGrane, the disclosure of which is totally incorporated herein by reference, discloses an aqueous ink composition comprising an aqueous liquid vehicle, a colorant, and an additive wherein, when the ink has been applied to a recording substrate in an image pattern and a substantial amount of the aqueous liquid vehicle has either evaporated from the ink image, hydrogen bonds of sufficient strength exist between the additive molecules so that the additive forms hydrogen-bonded oligomers or polymers.

Copending Application U.S. Ser. No. 09/948,958, filed Sep. 7, 2001, U.S. Publication 20030105185, entitled "Phase Change Ink Compositions," with the named inventors H. Bruce Goodbrand, Thomas W. Smith, Dina Popovic, Daniel A. Foucher, and Kathleen M. McGrane, the disclosure of which is totally incorporated herein by reference, discloses a phase change ink composition comprising a colorant and an ink vehicle, the ink being a solid at temperatures less than about 50° C. and exhibiting a viscosity of no more than about 20 centipoise at a jetting temperature of no more than about 160° C., wherein at a first temperature hydrogen bonds of sufficient strength exist between the ink vehicle molecules so that the ink vehicle forms hydrogen-bonded dimers, oligomers, or polymers, and wherein at a second temperature which is higher than the first temperature the hydrogen bonds between the ink vehicle molecules are sufficiently broken that fewer hydrogen-bonded dimers, oligomers, or polymers are present in the ink at the second temperature than are present in the ink at the first temperature, so that the viscosity of the ink at the second temperature is lower than the viscosity of the ink at the first temperature.

Copending Application U.S. Ser. No. 10/770,305, filed Feb. 2, 2004, U.S. Publication 20040158063, entitled "Alkylated Tetrakis(triaminotriazine) Compounds and Phase Change Inks Containing Same," with the named inventors Danielle C. Boils Boissier, Marcel P. Breton, Jule W. Thomas, Jr., Donald R. Titterington, Jeffery H. Banning, H. Bruce Goodbrand, James D. Wuest, Marie Ève Perron, Francis Monchamp, and Hugues Duval, the disclosure of which is totally incorporated herein by reference, discloses compounds of the formulae

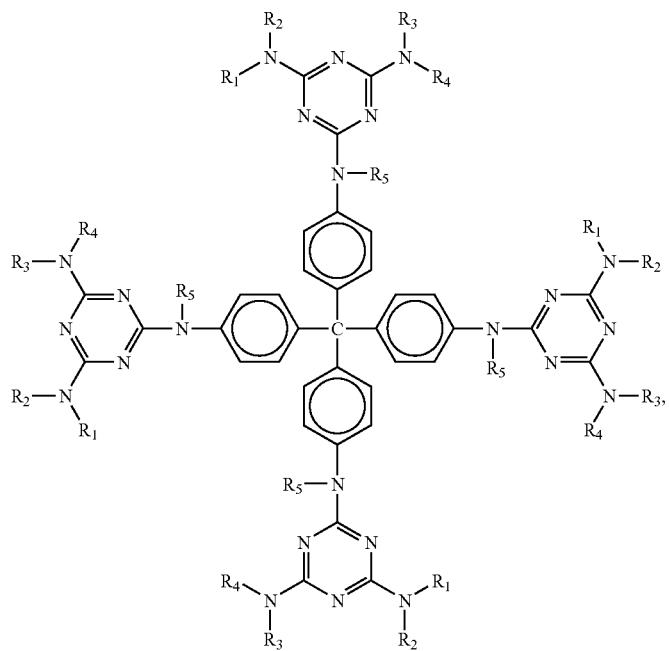

-continued

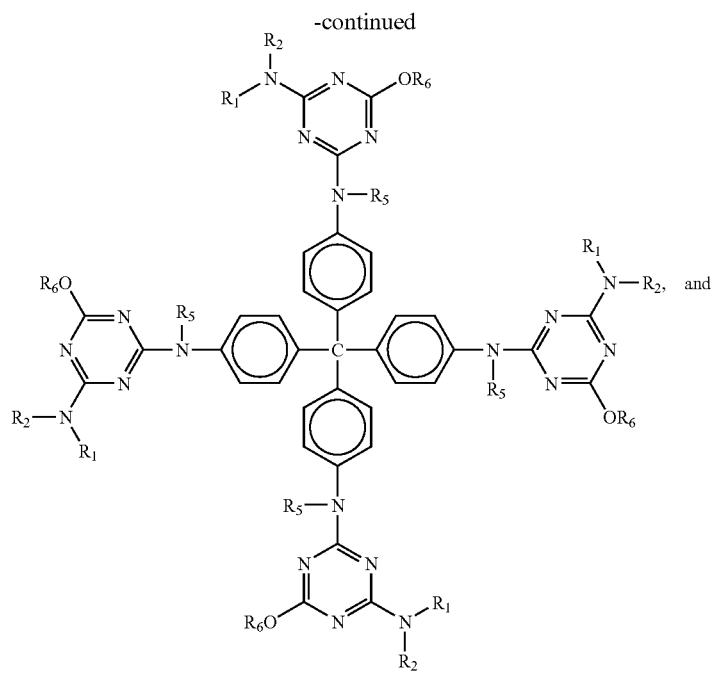

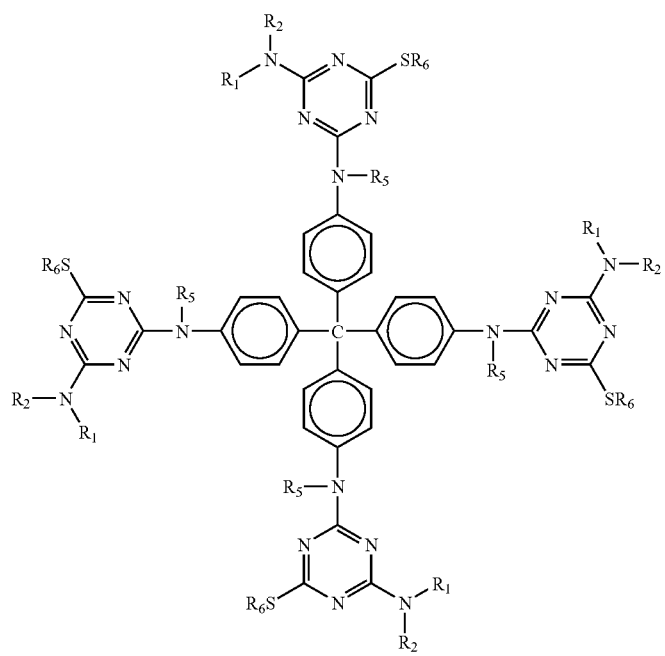

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group, (iii) an aryl group, (iv) an arylalkyl group, or (v) an alkylaryl group. Also disclosed are phase change ink compositions comprising a colorant and a phase change ink carrier comprising a material of this formula.

Copending Application U.S. Ser. No. 10/235,061, filed Sep. 4, 2002, U.S. Publication 20040060474, and Copending Application U.S. Ser. No. 10/794,930, filed Mar. 5, 2004, both entitled "Guanidinopyrimidinone Compounds and Phase Change Inks Containing Same," with the named inventors Danielle C. Boils-Boissier, Marcel P. Breton, Jule W. Thomas, Jr., Donald R. Titterington, Jeffery H. Banning, H. Bruce Goodbrand, James D. Wuest, Marie-Ève Perron, and Hugues Duval, the disclosure of which is totally incorporated herein by reference, discloses compounds of the formulae

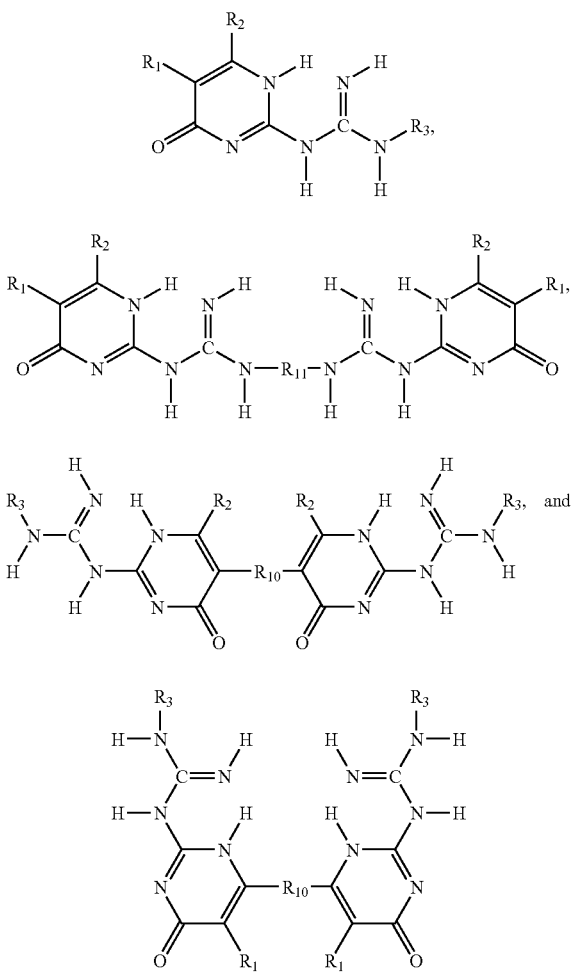

wherein, provided that at least one of $R_1$, $R_2$, and $R_3$ is not a hydrogen atom, $R_1$, $R_2$, and $R_3$ each, independently of the other, is (i) a hydrogen atom, (ii) an alkyl group, (iii) an aryl group, (iv) an arylalkyl group, or (v) an alkylaryl group, and wherein $R_1$ and $R_2$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula

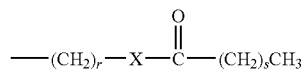

wherein r is an integer representing a number of repeat —$CH_2$— groups, wherein s is an integer representing a number of repeating —$CH_2$— groups, and wherein X is (a) a direct bond, (b) an oxygen atom, (c) a sulfur atom, (d) a group of the formula —$NR_{40}$— wherein $R_{40}$ is a hydrogen atom, an alkyl group, an aryl group, an arylalkyl group, or an alkylaryl group, or (e) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and $R_{10}$ and $R_{11}$ each, independently of the other, is (i) an alkylene group, (ii) an arylene group, (iii) an arylalkylene group, or (iv) an alkylarylene group, and wherein $R_{10}$ can also be (v) a polyalkyleneoxy group, (vi) a polyaryleneoxy group, (vii) a polyarylalkyleneoxy group, (viii) a polyalkylaryleneoxy group, (ix) a silylene group, (x) a siloxane group, (xi) a polysilylene group, or (xii) a polysiloxane group. Also disclosed are phase change ink compositions comprising a colorant and a phase change ink carrier comprising a material of this formula.

Copending Application U.S. Ser. No. 10/235,109, filed Sep. 4, 2002, U.S. Publication 20040075723, and Copending Application U.S. Ser. No. 10/810,370, filed Mar. 26, 2004, both entitled "Alkylated Urea and Triaminotriazine Compounds and Phase Change Inks Containing Same," with the named inventors Marcel P. Breton, Danielle C. Boils-Boissier, Jule W. Thomas, Jr., Donald R. Titterington, H. Bruce Goodbrand, Jeffery H. Banning, James D. Wuest, Dominic Laliberté, and Marie-Ève Perron, the disclosure of which is totally incorporated herein by reference, discloses compounds of the formulae

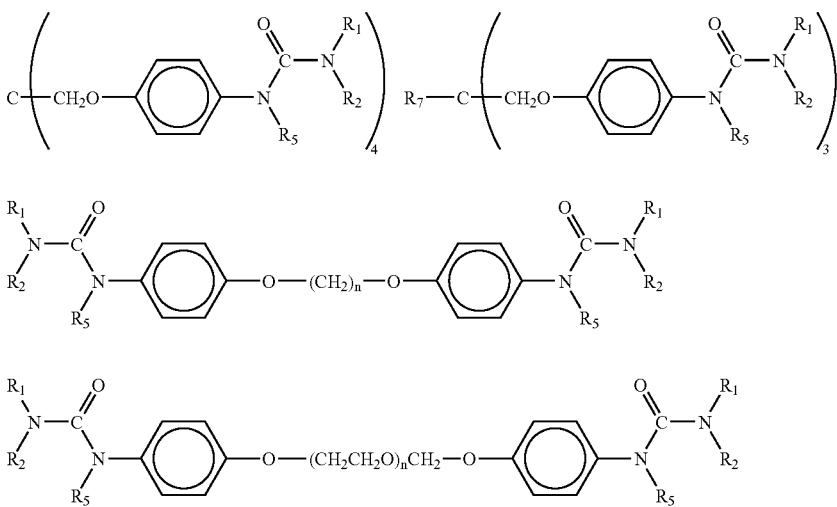

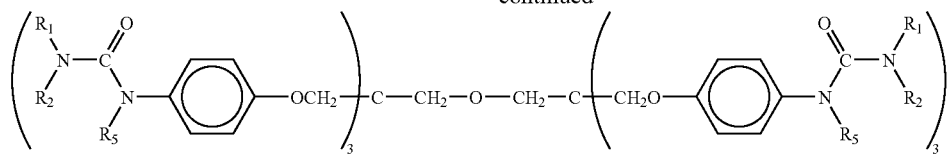

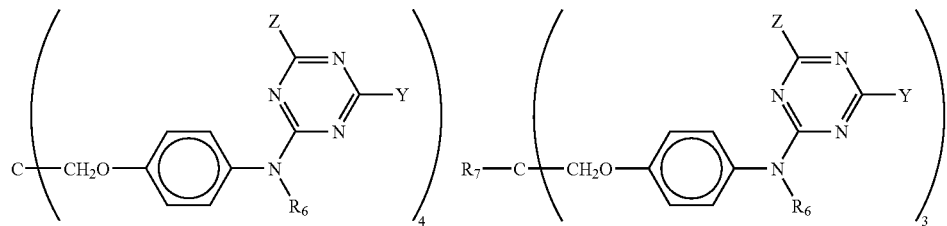

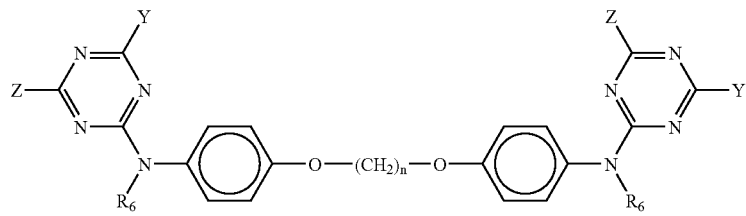

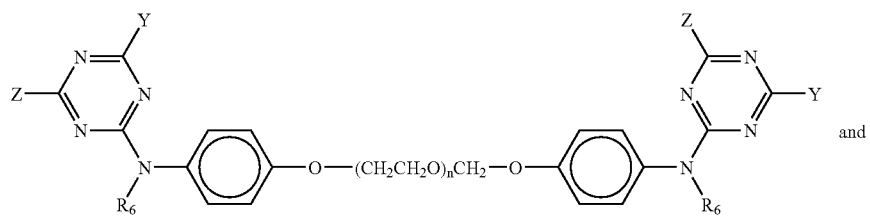

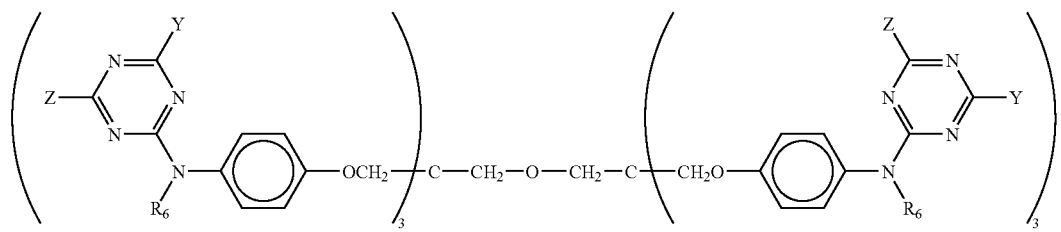

wherein Z is a group of the formula —OR$_1$, a group of the formula —SR$_1$, or a group of the formula —NR$_1$R$_2$, Y is a group of the formula —OR$_3$, a group of the formula —SR$_3$, or a group of the formula —NR$_3$R$_4$, n is an integer representing the number of repeat —(CH$_2$)— or —(CH$_2$CH$_2$O)— units, wherein, provided that at least one of R$_1$, R$_2$, R$_3$, R$_4$, R$_5$, and R$_6$ is a hydrogen atom, provided that at least one of R$_1$, R$_2$, R$_3$, R$_4$, R$_5$, and R$_6$ is other than a hydrogen atom, and provided that at least one Z or Y within the compound is a group of the formula —NR$_1$R$_2$ or a group of the formula —NR$_3$R$_4$, R$_1$, R$_2$, R$_3$, R$_4$, R$_5$, R$_6$, and R$_7$ each, independently of the others, is (i) a hydrogen atom, (ii) an alkyl group, (iii) an aryl group, (iv) an arylalkyl group, or (v) an alkylaryl group, and wherein R$_7$ can also be (vi) an alkoxy group, (vii) an aryloxy group, (viii) an arylalkyloxy group, (ix) an alkylaryloxy group, (x) a polyalkyleneoxy group, (xi) a polyaryleneoxy group, (xii) a polyarylalkyleneoxy group, (xiii) a polyalkylaryleneoxy group, (xiv) a silyl group, (xv) a siloxane group, (xvi) a polysilylene group, (xvii) a polysiloxane group, or (xviii) a group of the formula

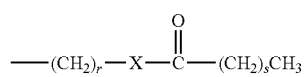

wherein r is an integer representing a number of repeat —CH$_2$— groups, wherein s is an integer representing a number of repeating —CH$_2$— groups, and wherein X is (a) a direct bond, (b) an oxygen atom, (c) a sulfur atom, (d) a group of the formula —NR$_{40}$— wherein R$_{40}$ is a hydrogen atom, an alkyl group, an aryl group, an arylalkyl group, or an alkylaryl group, or (e) a group of the formula —CR$_{50}$R$_{60}$— wherein R$_{50}$ and R$_{60}$ each, independently of the other, is a hydrogen atom, an alkyl group, an aryl group, an arylalkyl group, or an alkylaryl group, and wherein R$_6$ can also be

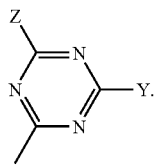

Also disclosed are phase change ink compositions comprising a colorant and a phase change ink carrier comprising a material of this formula.

Copending Application U.S. Ser. No. 10/235,125, filed Sep. 4, 2002, U.S. Publication 20040065227, entitled "Phase Change Inks Containing Gelator Additives," with the named inventors Marcel P. Breton, Danielle C. Boils-Boissier, Donald R. Titterington, Jule W. Thomas, Jr., Jeffery H. Banning, Christy Bedford, and James D. Wuest, the disclosure of which is totally incorporated herein by reference, discloses a phase change ink composition comprising an ink vehicle, a colorant, and a nonpolymeric organic gelator selected from the group consisting of anthracene-based compounds, steroid compounds, partially fluorinated high molecular weight alkanes, high molecular weight alkanes with exactly one hetero atom, chiral tartrate compounds, chiral butenolide-based compounds, bis-urea compounds, guanines, barbiturates, oxamide compounds, ureidopyrimidone compounds, and mixtures thereof, said organic gelator being present in the ink in an amount of no more than about 20 percent by weight of the ink, said ink having a melting point at or below which the ink is a solid, said ink having a gel point at or above which the ink is a liquid, and said ink exhibiting a gel state between the melting point and the gel point, said ink exhibiting reversible transitions between the solid state and the gel state upon heating and cooling, said ink exhibiting reversible transitions between the gel state and the liquid state upon heating and cooling, said melting point being greater than about 35° C., said gel point being greater than said melting point. Also disclosed are imaging processes employing phase change inks containing gelator additives.

BACKGROUND

Disclosed herein are bis(urea-urethane) compounds. More specifically, disclosed herein are some bis(urea-urethane) compounds and hot melt or phase change inks containing these compounds. One embodiment is directed to bis(urea-urethane) compounds of the formula

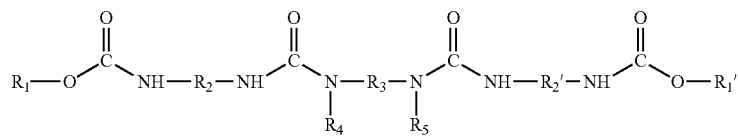

wherein R$_1$ and R$_1$' each, independently of the other, is an alkyl group selected from the group consisting of (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, and (31) cyclic ethylenically unsaturated substituted aliphatic groups containing hetero atoms, wherein at least one of R$_1$ and R$_1$' has at least about 6 carbon atoms, R$_2$ and R$_2$' each, independently of the other, is an alkylene group, wherein at least one of R$_2$ and R$_2$' has at least about 3 carbon atoms, R$_3$ is an alkylene group having at least about 2 carbon atoms, and $R_4$ and $R_5$ each, independently of the other, is a hydrogen atom or an alkyl group, and wherein $R_1$ and $R_1'$ each contain no more than 2 fully fluorinated carbon atoms.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 6,761,758 (Boils-Boissier et al.), the disclosure of which is totally incorporated herein by reference, discloses compounds of the formulae

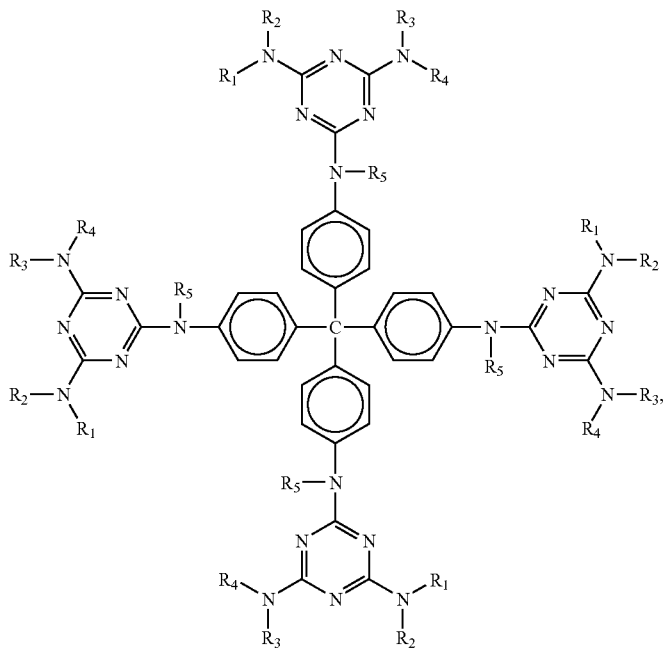

-continued

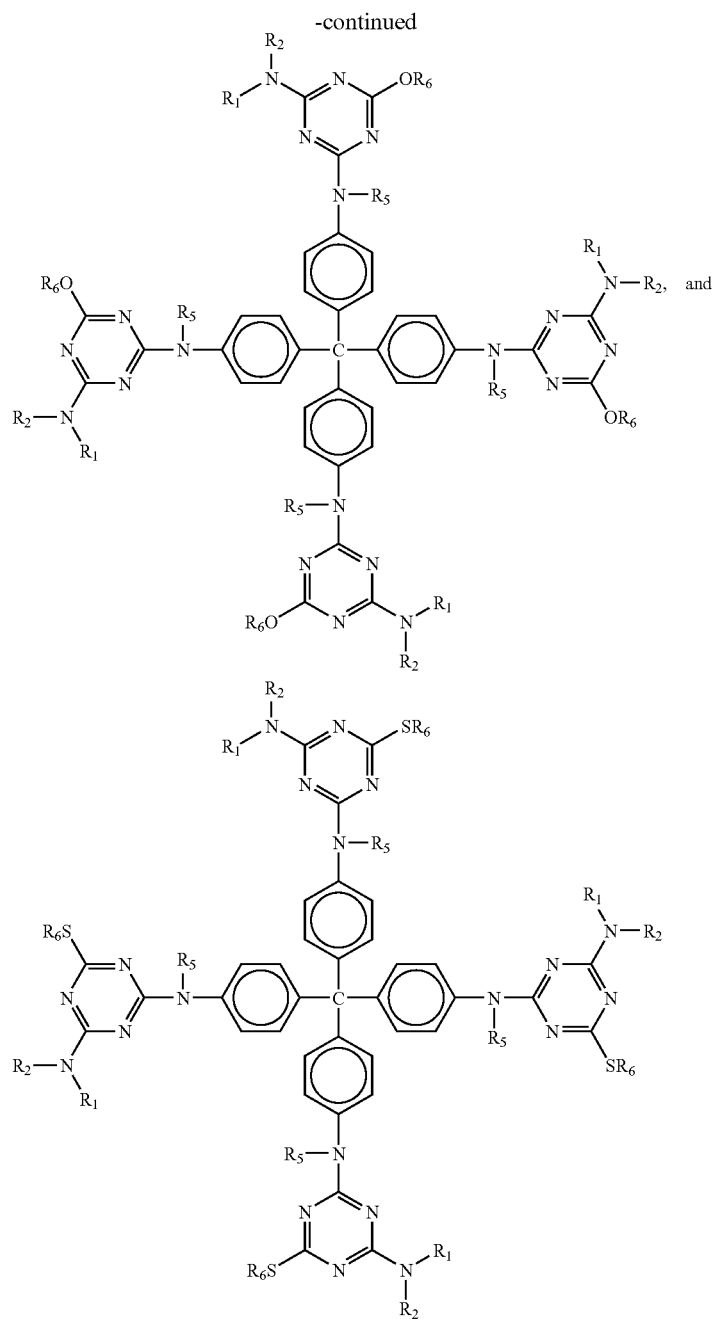

wherein, provided that at least one of $R_1$, $R_2$, $R_3$, $R_4$, $R_5$, and $R_6$ is a hydrogen atom, and provided that at least one of $R_1$, $R_2$, $R_3$, $R_4$, $R_5$, and $R_6$ is not a hydrogen atom, $R_1$, $R_2$, $R_3$, $R_4$, $R_5$, and $R_6$ each, independently of the others, is (i) a hydrogen atom, (ii) an alkyl group, (iii) an aryl group, (iv) an arylalkyl group, or (v) an alkylaryl group. Also disclosed are phase change ink compositions comprising a colorant and a phase change ink carrier comprising a material of this formula.

U.S. Pat. No. 6,471,758 and European Patent Publication EP 1 067 157 (Kelderman et al.), the disclosures of each of which are totally incorporated herein by reference, disclose an ink composition for a meltable ink usable in a printing device in which ink drops are ejected from ink ducts, which comprises agents which reversibly cross-link the ink, the said agents containing a gelling agent. When an ink drop which has been transferred to a substrate passes over into a gel during the cooling process, the consequence is that the viscosity of the melted ink drop increases greatly so that the drops become relatively immobile. In this way the ink drops are prevented from uncontrollably flowing into the paper. As a result, inks of this kind are suitable for use on both porous and smooth substrates. In addition, these inks have been found suitable for use in a printing device in which printed substrates are subjected to thermal after-treatment.

"Cyclic Bis-Urea Compounds as Gelators for Organic Solvents," J. van Esch et al., *Chem. Eur. J.* 1999, 5, No. 3, pp. 937-950, the disclosure of which is totally incorporated herein by reference, discloses the study of the gelation properties of bis-urea compounds derived from optically pure trans-1,2-diaminocyclohexane and 1,2-diaminobenzene, with pendant aliphatic, aromatic, or ester groups, as well as the structure of the resulting gels.

"The Design of Organic Gelators Based on a Family of Bis-Ureas," R. E. Meléndez et al., *Mat. Res. Soc. Symp. Proc.* 2000, 604, pp. 335-340, the disclosure of which is totally incorporated herein by reference, discloses a study of the organogelation properties of a family of bis-ureas.

"Formation of Organogels by Intermolecular Hydrogen Bonding Between Ureylene Segment," K. Hanabusa et al., *Chem. Lett.* 1996 pp. 885-886, the disclosure of which is totally incorporated herein by reference, discloses low molecular weight compounds having ureylene segment causing physical gelation in organic solvents. The main driving force for gelation was intermolecular hydrogen bonding between ureylene units.

"Low Molecular Weight Gelators for Organic Solvents," J. van Esch et al., in *Supramolecular Science: Where Is It and Where It Is Going*, R. Ungaro and E. Dalcanale, Eds., 1999, Netherlands: Kluwer Academic Publishers, pp. 233-259, the disclosure of which is totally incorporated herein by reference, discloses the gelation of solvents by organogelators.

"Organogels and Low Molecular Mass Organic Gelators," D. J. Abdallah and R. G. Weiss, *Adv. Mater.* 2000, 12, No. 17, September 1, pp. 1237-1247, the disclosure of which is totally incorporated herein by reference, discloses the stepwise simplification of low molecular-mass organic gelator structures and the development of methods to determine their packing in organogels at the micrometer-to-angstrom distance regimes, as well as an overview of current and potential applications for these materials.

"Remarkable Stabilization of Self-Assembled Organogels by Polymerization," M. de Loos et al., *J. Am. Chem. Soc.* 1997, 119, 12675-12676, the disclosure of which is totally incorporated herein by reference, discloses studies of polymerizable bis(amido)cyclohexane and bis(ureido)cyclohexane derivatives, investigating their gelating capacity for organic solvents.

"Low-molecular weight organogelators," P. Terech, in *Specialist Surfactants*, I. D. Robb, Ed., 1997, London: Chapman & Hall, pp. 208-68, the disclosure of which is totally incorporated herein by reference, discloses a special class of surfactants which have the ability to form viscoelastic fluids or solid-like materials in organic solvents at concentrations lower than about 2 percent.

"New Functional Materials Based on Self-Assembling Organogels: From Serendipity Towards Design," J. H. van Esch and B. L. Feringa, *Angew. Chem. Int. Ed.* 2000, 39, No. 13, pp. 2263-2266, the disclosure of which is totally incorporated herein by reference, discloses a review of developments in the field of organogels.

"Synthesis and Self-Assembling Properties of Polymerizable Organogelators," G. Wang and A. D. Hamilton, *Chem. Eur. J.* 2002, 8, No. 8, pp. 1954-1961, the disclosure of which is totally incorporated herein by reference, discloses the development of a family of polymerizable urea derivatives that are gelators for organic solvents.

"Low Molecular Mass Gelators of Organic Liquids and the Properties of their Gels," P. Terech and R. G. Weiss, *Chem. Rev.* 1997, 97, pp. 3133-3159, the disclosure of which is totally incorporated herein by reference, discloses a review of the properties of thermally-reversible viscoelastic liquidlike or solidlike organogels comprising an organic liquid and low concentrations of relatively low molecular mass gelator molecules.

"Towards a Phenomenological Definition of the Term 'Gel'," K. Amdal et al., *Polymer Gels and Networks*, 1993, 1, pp. 5-17, the disclosure of which is totally incorporated herein by reference, discusses existing definitions of the term "gel" and proposes specific uses of the term.

PCT Patent Publication WO 03/084508 and European Patent Publication EP 1 350 507 (Friesen et al.), the disclosures of each of which are totally incorporated herein by reference, disclose delivery vehicles for delivering a substance of interest to a predetermined site, said vehicle comprising said substance and a means for inducing availability of at least one compartment of said vehicle toward the exterior, thereby allowing access of said substance to the exterior of said vehicle at said predetermined site. The invention is further concerned with uses of said vehicle and methods for preparing it.

PTC Patent Publication WO 03/040135 (Dowle et al.), the disclosure of which is totally incorporated herein by reference, discloses compounds of the formula

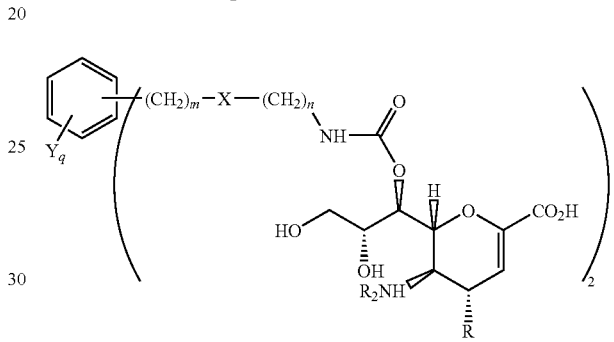

in which R is an amino or guanidino group, $R_2$ is acetyl or trifluoroacetyl, X is $CONH$, $SO_2NH$, $NHCO$, or $NHCONH$, m is either 0 or 1, n is an integer from 2 to 6, q is an integer from 0 to 3, and Y is hydrogen or an aromatic substituent, or a pharmaceutically acceptable derivative thereof. Also disclosed are methods for their preparation, pharmaceutical formulations containing them, and their use in the prevention or treatment of a viral infection.

PTC Patent Publication WO 00/55149 and U.S. Pat. No. 6,548,476 (Wu et al.), the disclosures of each of which are totally incorporated herein by reference, disclose dimeric compounds, methods for their preparation, pharmaceutical formulations thereof, and their use as antiviral agents. The compounds are particularly useful against influenza virus. In particular the references disclose a dimeric compound which comprises two neuraminidase binding groups attached to a spacer or linking group. Preferably the dimeric molecule comprises two neuraminidase-binding neuraminic acid (sialic acid) or cyclopentyl or cyclohexenyl carboxylic acid derivatives covalently attached to a common spacer group. Pharmaceutical compositions and methods of treatment, prophylaxis and diagnosis are disclosed and claimed.

U.S. Patent Publication 20010044553 (Kabashima et al.), the disclosure of which is totally incorporated herein by reference, discloses a urea-urethane compound having one or more urea groups and one or more urethane groups in the molecular structure, the number of said urea groups (A) and the number of said urethane groups (B) satisfying the following numerical formula: $10 \geq (A+B) \geq 3$ wherein each of A and B is an integer of 1 or more.

European Patent Publication EP 1 048 681 and U.S. Pat. No. 6,420,466 (Haubennestel et al.), the disclosures of each of which are totally incorporated herein by reference, disclose a process for preparing a solution that is active as a thixotropic agent and contains urea urethanes, in which monohydroxyl compounds are reacted with an excess of toluene diisocyanate, the unreacted portion of the toluene diisocyanate is removed from the reaction mixture, and the monoisocyanate adduct obtained is further reacted with diarines in the presence of a lithium salt to form urea urethanes. The invention also relates to the use of the solution for imparting thixotropic properties to coating compounds.

Japanese Patent Publication JP 10310633, the disclosure of which is totally incorporated herein by reference, discloses a cationic curing catalyst composition improved in stability during storage at room temperature or above and suppressed in increase in viscosity, using at least one stabilizer selected from the compounds containing a urethane bond, an amide bond, a urea bond and a carbodiimide group in the molecule and a dialkylaminopyridine compound or a proton acid compound.

European Patent Publication EP 0 056 153 and U.S. Pat. No. 4,384,102 (Rasshofer et al.), the disclosures of each of which are totally incorporated herein by reference, disclose compounds having both s-triazine units and epoxide groups present that are prepared by reacting an epoxide containing an isocyanate-reactive group with a triisocyanate corresponding to the formula

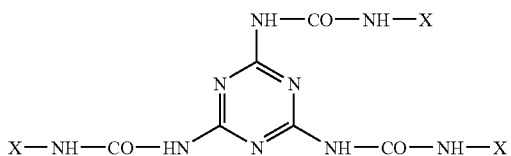

in which X is as defined therein. These reactants are used in quantities such that the equivalent ratio of isocyanate groups to isocyanate-reactive groups is maintained at less than or equal to 1 to 1. The compounds thus produced are particularly useful as reactive cross-linkers in the production of polyurethanes and polyepoxides.

European Patent Publication EP 0 160 402 and U.S. Pat. No. 4,566,981 (Howells), the disclosures of each of which are totally incorporated herein by reference, disclose cationic and non-ionic fluorochemicals, mixtures of cationic and non-ionic fluorochemicals, blends of the mixtures with fluorochemical poly(oxyalkylenes), and compositions of the fluorochemicals with hydrocarbon nonionic surfactants. These fluorochemicals and compositions, in dispersions, emulsions and microemulsions, may be applied to porous fibrous substrates to give oil and water repellency and soil resistance.

Japanese Patent Publication JP 59030919, the disclosure of which is totally incorporated herein by reference, discloses a method to prevent the bad influence of a treatment on spinning properties and drawing properties of synthetic yarn, by providing undrawn yarn of melt spinning with a spinning oil, applying a specific treatment to it, drawing and heat-treating it. The undrawn yarn which is prepared by melt spinning and cooled is provided with a spinning oil by the oil applicator, coated with a treatment by the treatment applicator, sent through the taking up roller and the drawing rollers, and wound around the winder. The treatment is a compound shown by the formula $(R_f\text{—}A\text{—}B_1\text{—}CONH\text{—}X\text{—}NHCO\text{—}B_2\text{—})_nY$ ($R_f$ is 4-16C perfluoroalkyl; A is $\text{—}(CH_2)_{x1}\text{—}$, $CON(R_1)\text{—}(CH_2)_{x2}\text{—}$, or $SO_2N(R_1)\text{—}(CH_2)_{x2}\text{—}$; x1 is 1-20 integer; x2 is 1-12 integer; $R_1$ is H, or 1-6C alkyl; $B_1$ and $B_2$ are $\text{—}O\text{—}$, $\text{—}S\text{—}$, or $\text{—}N(R_2)\text{—}$; $R_2$ is H, or 1-4C alkyl; X is bifunctional organic group; Y is polyfunctional organic group; n is 2-10 integer) and its pickup is 0.03-2.0 wt %.

Compounds that enable gelation are also disclosed in, for example: "Reversible Polymers Formed from Self-Complementary Monomers Using Quadruple Hydrogen Bonding," R. P. Sijbesma et al., *Science*, Vol. 278, p. 1601 (1997); "Supramolecular Polymers," R. Dagani, *Chemical and Engineering News*, p. 4 (December 1997); "Supramolecular Polymers from Linear Telechelic Siloxanes with Quadruple-Hydrogen-Bonded Units," J. H. K. Hirschberg et al., *Macromolecules*, Vol. 32, p. 2696 (1999); "Design and Synthesis of 'Smart' Supramolecular Liquid Crystalline Polymers via Hydrogen-Bond Associations," A. C. Griffin et al., *PMSE Proceedings*, Vol. 72, p. 172 (1995); "The Design of Organic Gelators: Solution and Solid State Properties of a Family of Bis-Ureas," Andrew J. Carr et al., *Tetrahedron Letters*, Vol. 39, p. 7447 (1998); "Hydrogen-Bonded Supramolecular Polymer Networks," Ronald F. M. Lange et al., *Journal of Polymer Science, Part A: Polymer Chemistry*, Vol. 37, p. 3657 (1999); "Combining Self-Assembly and Self-Association—Towards Columnar Supramolecular Structures in Solution and in Liquid-Crystalline Mesophase," Arno Kraff et al., *Polym. Mater. Sci. Eng.*, Vol. 80, p. 18 (1999); "Facile Synthesis of β-Keto Esters from Methyl Acetoacetate and Acid Chloride: The Barium Oxide/Methanol System," Y. Yuasa et al., *Organic Process Research and Development*, Vol. 2, p. 412 (1998); "Self-Complementary Hydrogen Bonding of 1,1'-Bicyclohexylidene-4,4'-dione Dioxime. Formation of a Non-Covalent Polymer," F. Hoogesteger et al., *Tetrahedron*, Vol. 52, No. 5, p. 1773 (1996); "Molecular Tectonics. Three-Dimensional Organic Networks with Zeolite Properties," X. Wang et al., *J. Am. Chem. Soc.*, Vol. 116, p. 12119 (1994); "Helical Self-Assembled Polymers from Cooperative Stacking of Hydrogen-Bonded Pairs," J. H. K. Ky Hirschberg et al., *Nature*, Vol. 407, p. 167 (2000); "New Supramolecular Arrays based on Interactions between Carboxylate and Urea Groups: Solid-State and Solution Behavior," Abdullah Zafar et al., *New J. Chem.*, 1998, 137-141; U.S. Pat. No. 6,320,018; U.S. Pat. No. 5,892, 116; PCT Patent Publication WO 97/24364; "The Unusual Molecular Organization of 2,3-Bis(n-hexyloxy)-anthracene in the Crystal. A Hint to the Origin of the Gelifying Properties of 2,3-Bis(n-alkyloxy)anthracenes?", J-L. Pozzo et al., *J. Chem. Soc., Perkin Trans.*, 2, 824-826 (2001); "The Quest for the Simplest Possible Organogelators and Some Properties of their Organogels," D. Abdallah et al., *J. Braz. Chem. Soc.*, Vol. 11, No. 3, 209-218 (2000); "Organogel Electrolytes Based on a Low Molecular Weight Gelator: 2,3-Bis(n-decyloxy)anthracene," F. Placin et al., *Chem. Mater.* 13, 117-121 (2001); "Novel Vesicular Aggregates of Crown-Appended Cholesterol Derivatives Which Act as Gelators of Organic Solvents and as Templates for Silica Transcription," J. Jung et al., *J. Am. Chem. Soc.*, Vol. 122, No. 36, 8648-8653 (2000); "n-Alkanes Gel n-Alkanes (and Many Other Organic Liquids)," D. Abdallah et al., *Langmuir*, 16, 352-355 (2000); "Low Molecular Mass Gelators of Organic Liquids and the Properties of their Gels," P. Terech et al., *Chem. Rev.*, 97, 3133-3159 (1997); "Organogels and Low Molecular Mass Organic Gelators," D. Abdallah et al., *Adv. Mater.*, 12, No. 17, 1237 (2000); "Making it All Stick Together: the Gelation of Organic Liquids by Small Organic Molecules," F. Schoonbeek, Doctoral Thesis, U. of Groningen, Netherlands, April 2001; Twieg et al., *Macromolecules*, Vol. 18, p. 1361 (1985); "Synthesis and Reactions of Polyhydric Alcohols I. Synthesis and Reactions of p-Toluenesulfonates of Polyhydric Alcohols," *Zhurnal Obshchei Khimii*, Vol. 35, No. 5, p. 804-807 (1965); "The Chemotherapy of Schistosomiasis. Part I. Derivatives and Analogs of αω-Di-(p-aminophenoxy)alkanes," J. Ashley et al., *J. Chem. Soc.* 1958, 3293; "Remarkably Simple Small Organogelators: Di-n-alkoxy-benzene Derivatives," G. Clavier et al., *Tetrahedron Letters*, 40, 9021-9024 (1999); "Rational Design of Low Molecular Mass Organogelators: Toward a Library of Functional N-Acyl-1-ω-Amino Acid Derivatives," G. Mieden-Gundert et al., *Angew. Chem. Int. Ed.*, 40, No. 17, 3164-3166 (2001); U.S. Pat. No. 2,703,808; "Rational Design of New Acid-Sensitive Organogelators," J-L. Pozzo et al., *J. Mater. Chem.*, Vol. 8, pp. 2575-2577 (1998); J. T. Thurston et al., *J. Am. Chem. Soc.*, Vol. 73, pp. 2981-3008 (1951); *J. Am. Chem. Soc.*, Vol. 96, pp. 1082-1087 (1974); J-L. Pozzo et al., *Tetrahedron*, Vol. 53, No. 18, pp. 6377-6390 (1997); J-L. Pozzo et al., *Mol. Cryst. Liq. Cryst.*, Vol. 344, pp. 101-106 (2000); Y. C. Lin, R. G. Weiss, *Macromolecules*, Vol. 20, p. 414 (1987); U.S. Pat. No. 4,790,961; Murata et al, *J. Am. Chem. Soc.*, Vol. 116, No 15, pp. 6664-6676 (1994); A. Ikeda et al., *Rep. Asahi Glass Found. Ind. Technol.*, Vol. 61, p. 115, (1992); Rabolt et al., *Macromolecules*, Vol. 17, p. 2786 (1984); D. J. Abdallah et al., *Chem. Mater.*, Vol. 11, p. 2907 (1999); Ralston et al., *J. Org. Chem.*, Vol. 9, p. 259 (1944); L. Lu et al., *Chem. Commun.*, 1996, p. 2029; *J. Prakt. Chem.*, Vol. 327 (3), pp. 383-98 (1985); B. L. Feringa et al., *J. Org. Chem.*, Vol. 53, p. 1125 (1988); J. C. DeJong et al., *Tetrahedron Lett.*, Vol. 30, p. 7239 (1989); J. C. DeJong, Ph.D. thesis, University of Groningen, The Netherlands, 1991; F. A. Neugebauer et al., *Chem. Ber.*, 1976, 109, 2389; U. Zehavi et al., *J. Org. Chem.*, Vol. 26, pp. 1097-1101 (1961); J. March, *Advanced Organic Chemistry*, 4th Edition, pp. 903 and 1091-1092, Wiley Interscience (New York 1992); J. Crossley Maxwell, *Aust. J. Chem.*, Vol. 47, pp. 723-738 (1994); V. J. Wotring et al., *Analytical Chemistry*, Vol. 62, No. 14, pp. 1506-1510 (1990); Tabushi et al., *J. Am. Chem. Soc.*, Vol. 103, pp. 6152-6157 (1981); T. Giorgi et al., "Gel-like lyomesophases formed in organic solvents by self-assembled guanine ribbons," *Chemistry—A European Journal* (2002), 8(9), 2143-2152; T. Suyama et al., "A method for the preparation of substituted biguanides," *Nippon Kagaku Kaishi* (1989), (5), 884-7; Polish Patent Publication PL 148060 B1; Polish Patent Publication PL 134682 B1; C. S. Snijder et al., *Chem. Eur. J.*, Vol. 1, No. 9, pp. 594-597 (1995); S. Senda et al., Gifu Coll. Pharm., Gifu, Japan. *Yakugaku Zasshi* (1969), 89 (2), 254-259; B. Gluncic et al, *Acta Pharm. Jugosl.* (1986), 36(4), 393-404; Canadian Patent Publication CA 941377; M. Klein, Recent Dev. Mass Spectrom. Biochem. Med., [Proc. Int. Symp.], 4th (1978), Meeting Date 1977, 1, 471-82; PCT Patent Publication WO/9011283; Japanese Patent Publication JP 62181279; T. Wada et al., "A New Boranophosphorylation Reaction for the Synthesis of Deoxyribonucleoside Boranophosphates," *Tetrahedron Letters*, Vol. 43, No. 23, pp. 4137-4140 (2002); R. Schirrmacher et al., "Dimethylpyridin-4-ylamine-catalysed alcoholysis of 2-amino-N,N,N-trimethyl-9H-purine-6-ylammonium chloride: An effective route to O6-substituted guanine derivatives from alcohols with poor nucleophilicity," *Synthesis*, Vol. 4, pp. 538-542 (2002); Z. Situ, "Synthesis of Tricyclic Derivatives of Guanine Analogue Catalyzed by KF—Al$_2$O$_3$," *Huaxue Shiji*, Vol. 24, No. 1, p. 57 (2002); Korean Patent 2000003081 (Korean Patent Application KR 1998-24185); S. Bailey et al., "Synthesis and Antiviral Activity of 9-Alkoxypurines: New 9-(Hydroxyalkoxy) Derivatives of Guanine and 8-Methylguanine," *Antiviral Chem. Chemother.*, Vol. 5, No. 1, pp. 21-33 (1994); Japanese Patent Publication JP 06157529; Japanese Patent Publication JP 3217541; M. R. Harnden et al., "Synthesis, Oral Bioavailability and In Vivo Activity of Acetal Derivatives of the Selective Antiherpesvirus Agent 9-(3-Hydroxypropoxy)Guanine (BRL44385)," *Antiviral Chem. Chemother.*, Vol. 5, No. 3, pp. 147-54 (1994); Spanish Patent Publication ES 2047457; B. K. Bhattacharya et al., "Synthesis of Certain N- and C-alkyl Purine Analogs," *J. Heterocycl. Chem.*, Vol. 30, No. 5, pp. 1341-9 (1993); Polish Patent Publication PL 148969; PCT Patent Publication WO/9011283; U.S. Pat. No. 5,298,618; and Japanese Patent Publication JP 62181279, the disclosures of each of which are totally incorporated herein by reference.

Known organogelator compounds containing two or more urea functional groups exhibit some disadvantages for performing in a phase-change solid ink vehicle, such as high melting point and high degree of crystallinity.

Many currently used phase change inks require high jetting temperatures of about 140° C. or greater and also require relatively long warmup times for the printer. In addition, many currently used phase change inks generate images with relatively poor scratch resistance and relatively poor image permanence.

While known compositions and processes are suitable for their intended purposes, a need remains for improved phase change ink compositions. In addition, a need remains for phase change inks that can be jetted at reduced temperatures of about 110° C. or lower, thereby enabling cost and energy savings. Further, a need remains for phase change inks that enable printing with reduced printer warm-up times. Additionally, a need remains for phase change inks that generate images with improved scratch resistance. There is also a need for phase change inks that generate images with improved image permanence. In addition, there is a need for phase change inks that generate images with improved image quality. Further, there is a need for phase change inks that exhibit the aforementioned advantages when used in a printing process wherein the ink is first jetted onto an intermediate transfer member and subsequently transferred from the intermediate transfer member to a final print substrate such as plain or coated paper or a transparency. Additionally, there is a need for phase change inks that exhibit the aforementioned advantages when used in a printing process wherein the ink is jetted directly onto a final print substrate such as plain or coated paper or a transparency. A need also remains for phase change inks that exhibit the aforementioned advantages when used in printing processes at relatively high speeds. In addition, a need remains for phase change inks having desirably low melting points that also contain gelator compounds which enable additional advantages in the phase change inks. Further, a need remains for gelator compounds for use in phase change inks and other applications that have a desirably low degree of crystallinity. Additionally, a need remains for gelator compounds that are soluble in phase change ink carriers. There is also a need for phase change inks that exhibit an intermediate gel phase between the solid phase and the liquid phase. In addition, there is a need for phase change inks exhibiting an intermediate gel phase wherein the gel phase transition is desirably narrow. Further, there is a need for gelator compounds that enable desirably narrow gel phase transitions. Additionally, there is a need for phase change inks exhibiting an intermediate gel phase wherein the gel phase transition entails a tan-delta of less than about 10. A need also remains for gelator compounds that enable gel phase transitions entailing a tan-delta of less than about 10. In addition, a need remains for gelator compounds that are less highly crystalline and do not pack as tightly within a molecular network as do more crystalline materials, thereby enabling them to be soluble within molten phase change inks.

SUMMARY

Disclosed herein are bis(urea-urethane) compounds of the formula

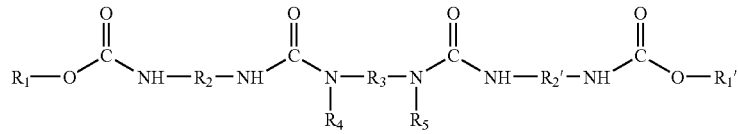

wherein $R_1$ and $R_1'$ each, independently of the other, is an alkyl group selected from the group consisting of (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, and (31) cyclic ethylenically unsaturated substituted aliphatic groups containing hetero atoms, wherein at least one of $R_1$ and $R_1'$ has at least about 6 carbon atoms, $R_2$ and $R_2'$ each, independently of the other, is an alkylene group, wherein at least one of $R_2$ and $R_2'$ has at least about 3 carbon atoms, $R_3$ is an alkylene group having at least about 2 carbon atoms, and $R_4$ and $R_5$ each, independently of the other, is a hydrogen atom or an alkyl group, and wherein $R_1$ and $R_1'$ each contain no more than 2 fully fluorinated carbon atoms.

DETAILED DESCRIPTION

The bis(urea-urethane) compounds are of the formula

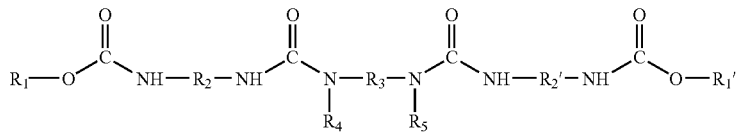

wherein $R_1$ and $R_1'$ each, independently of the other, is an alkyl group (including linear, branched, saturated, unsaturated, cyclic, substituted, and unsubstituted alkyl groups, and wherein hetero atoms, such as oxygen, nitrogen, sulfur, silicon, phosphorus, boron, and the like either may or may not be present in the alkyl group), said alkyl group being selected from the group consisting of: (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, and (31) cyclic ethylenically unsaturated substituted aliphatic groups containing hetero atoms, in one embodiment with at least 1 carbon atom, in another embodiment with at least about 4 carbon atoms, and in yet another embodiment with at least about 10 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, $R_2$ and $R_2'$ each, independently of the other, is an alkylene group (including linear, branched, saturated, unsaturated, cyclic, substituted, and unsubstituted alkylene groups, and wherein hetero atoms, such as oxygen, nitrogen, sulfur, silicon, phosphorus, boron, and the like either may or may not be present in the alkylene group), in one embodiment with at least about 2 carbon atoms, in another embodiment with at least about 4 carbon atoms, and in yet another embodiment with at least about 6 carbon atoms, and in one embodiment with no more than about 100 carbon atoms, in another embodiment with no more than about 60 carbon atoms, and in yet another embodiment with no more than about 30 carbon atoms, although the number of carbon atoms can be outside of these ranges, including (but not limited to) (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, (31) cyclic ethylenically unsaturated substituted aliphatic groups containing hetero atoms, and (32) aliphatic groups containing both cyclic and acyclic portions, said aliphatic groups being ethylenically unsaturated, substituted, and containing hetero atoms, $R_3$ is an alkylene group (including linear, branched, saturated, unsaturated, cyclic, substituted, and unsubstituted alkylene groups, and wherein hetero atoms, such as oxygen, nitrogen, sulfur, silicon, phosphorus, boron, and the like either may or may not be present in the alkylene group), in one embodiment with at least about 2 carbon atoms, in another embodiment with at least about 4 carbon atoms, in yet another embodiment with at least about 6 carbon atoms, in still another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with about 20 carbon atoms, in another embodiment with at least about 22 carbon atoms, in yet another embodiment with at least about 24 carbon atoms, in still another embodiment with about 26 carbon atoms, in another embodiment with at least about 28 carbon atoms, in yet another embodiment with at least about 30 carbon atoms, in still another embodiment with about 32 carbon atoms, in another embodiment with at least about 34 carbon atoms, and in yet another embodiment with at least about 36 carbon atoms, and in one embodiment with no more than about 200 carbon atoms, in another embodiment with no more than about 100 carbon atoms, and in yet another embodiment with no more than about 50 carbon atoms, although the number of carbon atoms can be outside of these ranges, including (but not limited to) (1) linear saturated unsubstituted aliphatic groups containing no hetero atoms, (2) branched saturated unsubstituted aliphatic groups containing no hetero atoms, (3) cyclic saturated unsubstituted aliphatic groups containing no hetero atoms, (4) aliphatic groups containing both cyclic and acyclic portions, said aliphatic groups being saturated, unsubstituted, and containing no hetero atoms, (5) linear ethylenically unsaturated unsubstituted aliphatic groups containing no hetero atoms, (6) branched ethylenically unsaturated unsubstituted aliphatic groups containing no hetero atoms, (7) cyclic ethylenically unsaturated unsubstituted aliphatic groups containing no hetero atoms, (8) aliphatic groups containing both cyclic and acyclic portions, said aliphatic groups being ethylenically unsaturated, unsubstituted, and containing no hetero atoms, (9) linear saturated substituted aliphatic groups containing no hetero atoms, (10) branched saturated substituted aliphatic groups containing no hetero atoms, (11) cyclic saturated substituted aliphatic groups containing no hetero atoms, (12) aliphatic groups containing both cyclic and acyclic portions, said aliphatic groups being saturated, substituted, and containing no hetero atoms, (13) linear ethylenically unsaturated substituted aliphatic groups containing no hetero atoms, (14) branched ethylenically unsaturated substituted aliphatic groups containing no hetero atoms, (15) cyclic ethylenically unsaturated substituted aliphatic groups containing no hetero atoms, (16) aliphatic groups containing both cyclic and acyclic portions, said aliphatic groups being ethylenically unsaturated, substituted, and contain no hetero atoms, (17) linear saturated unsubstituted aliphatic groups containing hetero atoms, (18) branched saturated unsubstituted aliphatic groups containing hetero atoms, (19) cyclic saturated unsubstituted aliphatic groups containing hetero atoms, (20) aliphatic groups containing both cyclic and acyclic portions, said aliphatic groups being saturated, unsubstituted, and containing hetero atoms, (21) linear ethylenically unsaturated unsubstituted aliphatic groups containing hetero atoms, (22) branched ethylenically unsaturated unsubstituted aliphatic groups containing hetero atoms, (23) cyclic ethylenically unsaturated unsubstituted aliphatic groups containing hetero atoms, (24) aliphatic groups containing both cyclic and acyclic portions, said aliphatic groups being ethylenically unsaturated, unsubstituted, and containing hetero atoms, (25) linear saturated substituted aliphatic groups containing hetero atoms, (26) branched saturated substituted aliphatic groups containing hetero atoms, (27) cyclic saturated substituted aliphatic groups containing hetero atoms, (28) aliphatic groups containing both cyclic and acyclic portions, said aliphatic groups being saturated, substituted, and containing hetero atoms, (29) linear ethylenically unsaturated substituted aliphatic groups containing hetero atoms, (30) branched ethylenically unsaturated substituted aliphatic groups containing hetero atoms, (31) cyclic ethylenically unsaturated substituted aliphatic groups containing hetero atoms, and (32) aliphatic groups containing both cyclic and acyclic portions, said aliphatic groups being ethylenically unsaturated, substituted, and containing hetero atoms, and $R_4$ and $R_5$ each, independently of the other, is a hydrogen atom or an alkyl group (including linear, branched, saturated, unsaturated, substituted, and unsubstituted alkyl groups), in one embodiment with at least 1 carbon atom, and in one embodiment with no more than about 3 carbon atoms, although the number of carbon atoms can be outside of these ranges, wherein the substituents on the substituted alkyl and alkylene groups in $R_1$, $R_1'$, $R_2$, $R_2'$, $R_3$, $R_4$, and $R_5$ can be (but are not limited to) halogen atoms, including fluorine, chlorine, bromine, and iodine atoms, imine groups, ammonium groups, cyano groups, pyridinium groups, ether groups, aldehyde groups, ketone groups, ester groups, carbonyl groups, thiocarbonyl groups, sulfide groups, sulfoxide groups, phosphine groups, nitrile groups, mercapto groups, nitro groups, nitroso groups, sulfone groups, acyl groups, urethane groups, urea groups, mixtures thereof, and the like, wherein two or more substituents can be joined together to form a ring.

In one specific embodiment, $R_1$ and $R_1'$ are the same. In another specific embodiment, $R_2$ and $R_2'$ are the same. In yet another specific embodiment, $R_4$ and $R_5$ are both hydrogen. In still another embodiment, $R_1$ and $R_1'$ are the same and $R_2$ and $R_2'$ are the same. In yet still another specific embodiment, $R_1$ and $R_1'$ are the same, $R_2$ and $R_2'$ are the same, and $R_4$ and $R_5$ are both hydrogen.

Since hetero atoms can be included in the $R_1$ and $R_1'$ groups, $R_1$ and $R_1'$ also include alkoxy, polyalkyleneoxy, alkoxyalkyl, pyrrolidine, imidazole, pyrimidinone, oxazoline, thiazoline, and like groups, provided that no oxygen atom is directly bonded to one of the —NH— groups. In addition, since hetero atoms can be included in the $R_1$ and $R_1'$ groups, $R_1$ and $R_1'$ also include aliphatic heterocyclic groups.

Since hetero atoms can be included in the $R_2$ and $R_2'$ groups, $R_2$ and $R_2'$ also include alkyleneoxy, polyalkyleneoxy, alkoxyalkylene, pyrrolidine, imidazole, pyrimidinone, oxazoline, thiazoline, and like groups, provided that no oxygen atom is directly bonded to one of the nitrogen atoms. In addition, since hetero atoms can be included in the $R_2$ and $R_2'$ groups, $R_2$ and $R_2'$ also include aliphatic heterocyclic groups.

Since hetero atoms can be included in the $R_3$ group, $R_3$ also includes alkyleneoxy, polyalkyleneoxy, alkoxyalkylene, pyrrolidine, imidazole, pyrimidinone, oxazoline, thiazoline, and like groups, provided that no oxygen atom is directly bonded to one of the nitrogen atoms. In addition, since hetero atoms can be included in the $R_3$ group, $R_3$ also includes aliphatic heterocyclic groups.

At least one of $R_1$ and $R_1'$ have in one embodiment at least about 6 carbon atoms, in another embodiment at least about 8 carbon atoms, in yet another embodiment at least about 10 carbon atoms, in still another embodiment at least about 12 carbon atoms, in another embodiment at least about 14 carbon atoms, in yet another embodiment at least about 16 carbon atoms, and in still another embodiment at least about 18 carbon atoms, although the number of carbon atoms can be outside of these ranges. In another specific instance, $R_1$ and $R_1'$ each have in one embodiment at least about 6 carbon atoms, in another embodiment at least about 8 carbon atoms, in yet another embodiment at least about 10 carbon atoms, in still another embodiment at least about 12 carbon atoms, in another embodiment at least about 14 carbon atoms, in yet another embodiment at least about 16 carbon atoms, and in still another embodiment at least about 18 carbon atoms, although the number of carbon atoms can be outside of these ranges.

In one specific instance, $R_1$ and $R_1'$ each have in one embodiment no more than about 50 carbon atoms, in another embodiment no more than about 30 carbon atoms, and in yet another embodiment no more than about 18 carbon atoms, although the number of carbon atoms can be outside of these ranges.

At least one of $R_2$ and $R_2'$ have in one embodiment at least about 3 carbon atoms, in another embodiment at least about 4 carbon atoms, in yet another embodiment at least about 5 carbon atoms, and in still another embodiment at least about 6 carbon atoms, although the number of carbon atoms can be outside of these ranges. In another specific instance, $R_2$ and $R_2'$ each have in one embodiment at least about 3 carbon atoms, in another embodiment at least about 4 carbon atoms, in yet another embodiment at least about 5 carbon atoms, and in still another embodiment at least about 6 carbon atoms, although the number of carbon atoms can be outside of these ranges.

of a catalyst, and optionally in the presence of a solvent. Thereafter, the resulting product can be cooled to about room temperature and reacted with about 2 moles of product per every 1 mole of a diamine of the formula

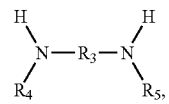

optionally in the presence of a solvent, at room temperature. The reaction proceeds as follows:

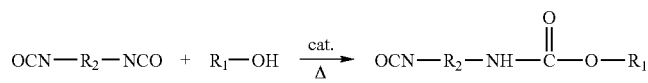

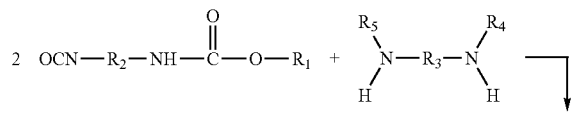

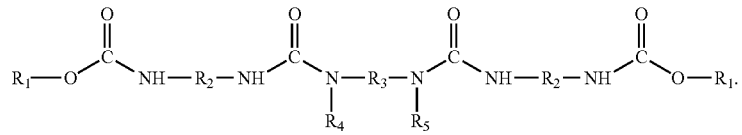

In one specific instance, $R_2$ and $R_2'$ each have in one embodiment no more than about 50 carbon atoms, in another embodiment no more than about 36 carbon atoms, and in yet another embodiment no more than about 12 carbon atoms, although the number of carbon atoms can be outside of these ranges.

$R_1$ and $R_1'$ each contain no more than 2 fully fluorinated carbon atoms. By "fully fluorinated carbon atoms" is meant that a carbon atom either is bonded to one other atom (other than fluorine, such as carbon, oxygen, nitrogen, or the like) and has three fluorine atoms bonded thereto, or is bonded to two other atoms (other than fluorine, such as carbon, oxygen, nitrogen, or the like) and has two fluorine atoms bonded thereto. Or, in other words, a "fully fluorinated carbon atom" is a —$CF_3$ group or a —$CF_2$— group. No more than two of such groups are present in $R_1$, and no more than two of such groups are present in $R_1'$. In one specific embodiment, $R_1$ and $R_1'$ each contain no more than 1 fully fluorinated carbon atom. In another specific embodiment, $R_1$ and $R_1'$ each contain no fully fluorinated carbon atoms. In yet another specific embodiment, $R_1$ and $R_1'$ each contain no fluorine atoms. In still another embodiment, $R_1$, $R_1'$, $R_2$, and $R_2'$ contain no fluorine atoms. In another embodiment, $R_1$, $R_1'$, $R_2$, $R_2'$, and $R_3$ contain no fluorine atoms. In yet another embodiment, $R_1$, $R_1'$, $R_2$, $R_2'$, $R_3$, $R_4$, and $R_5$ contain no fluorine atoms.

The bis(urea-urethane) compounds can be prepared by any desired or effective method. For example, a monoalcohol of the formula $R_1$—OH can be reacted with a diisocyanate of the formula OCN—$R_2$—NCO in approximately equimolar amounts at elevated temperatures, optionally in the presence Compounds wherein $R_1$ differs from $R_1'$ and/or wherein $R_2$ differs from $R_2'$ can be prepared by preparing two different compounds namely

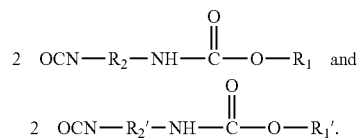

The monoalcohol and the diisocyanate are present in any desired or effective relative amounts, in one embodiment at least about 0.4 mole of monoalcohol per every one mole of diisocyanate, in another embodiment at least about 0.6 mole of monoalcohol per every one mole of diisocyanate, and in yet another embodiment at least about 0.8 mole of monoalcohol per every one mole of diisocyanate, and in one embodiment no more than about 1.4 moles of monoalcohol per every one mole of diisocyanate, in another embodiment no more than about 1.2 moles of monoalcohol per every one mole of diisocyanate, and in yet another embodiment no more than about 1 mole of monoalcohol per every one mole of diisocyanate, although the relative amounts can be outside of these ranges.

Examples of suitable catalysts include (but are not limited to) Lewis acid catalysts such as dibutyl tin dilaurate, bismuth tris-neodecanoate, cobalt benzoate, lithium acetate, stannous octoate, triethylamine, ferric chloride, aluminum trichloride, boron trichloride, boron trifluoride, titanium tetrachloride, tin tetrachloride, and the like. The catalyst, when present, is present in any desired or effective amount, in one embodiment at least about 0.2 mole percent, in another embodiment at least about 0.5 mole percent, and in yet another embodiment at least about 1 mole percent, and in one embodiment no more than about 10 mole percent, in another embodiment no more than about 7.5 mole percent, and in yet another embodiment no more than about 5 mole percent, based on the amount of diisocyanate, although the amount can be outside of these ranges.

Examples of suitable solvents for the first part of the reaction include (but are not limited to) toluene, hexane, heptane, methylene chloride, tetrahydrofuran, diethyl ether, ethyl acetate, methyl ethyl ketone, and the like, as well as mixtures thereof. When present, the solvent is present in any desired amount, in one embodiment at least about 10 milliliters per millimole of diisocyanate, in another embodiment at least about 20 milliliters per millimole of diisocyanate, in another embodiment at least about 30 milliliters per millimole of diisocyanate, and in one embodiment no more than about 100 milliliters per millimole of diisocyanate, in another embodiment no more than about 80 milliliters per millimole of diisocyanate, and in yet another embodiment no more than about 50 milliliters per millimole of diisocyanate, although the amount can be outside of these ranges.

The diisocyanate and the monoalcohol are heated to any desired or effective temperature, in one embodiment at least about 25° C., in another embodiment at least about 40° C., and in yet another embodiment at least about 50° C., and in one embodiment no more than about 125° C., in another embodiment no more than about 100° C., and in yet another embodiment no more than about 75° C., although the amounts can be outside of these ranges.

The diisocyanate and the monoalcohol are heated for any desired or effective period of time, in one embodiment at least about 5 minutes, in another embodiment at least about 10 minutes, and in yet another embodiment at least about 15 minutes, and in one embodiment no more than about 80 minutes, in another embodiment no more than about 40 minutes, and in yet another embodiment no more than about 30 minutes, although the time can be outside of these ranges.

Subsequent to the reaction between the diisocyanate and the monoalcohol, the first reaction product need not be recovered; the reaction mixture can be cooled to room temperature and the diamine can be added to the reaction mixture, along with additional solvent if desired, to complete the reaction.

The first reaction product and the diamine are present in any desired or effective relative amounts, in one embodiment at least about 1.75 moles of first reaction product per every one mole of diamine, in another embodiment at least about 1.9 moles of first reaction product per every one mole of diamine, and in yet another embodiment at least about 2 moles of first reaction product per every one mole of diamine, and in one embodiment no more than about 2.3 moles of first reaction product per every one mole of diamine, in another embodiment no more than about 2.1 moles of first reaction product per every one mole of diamine, and in yet another embodiment no more than about 2 moles of first reaction product per every one mole of diamine, although the relative amounts can be outside of these ranges.

The first reaction product and the diamine are allowed to react at any desired or effective temperature, in one embodiment at least about 10° C., in another embodiment at least about 20° C., and in yet another embodiment at least about 30° C., and in one embodiment no more than about 75° C., in another embodiment no more than about 50° C., and in yet another embodiment no more than about 40° C., although the temperature can be outside of these ranges.

The first reaction product and the diamine are allowed to react for any desired or effective period of time, in one embodiment at least about 5 minutes, in another embodiment at least about 10 minutes, and in yet another embodiment at least about 20 minutes, and in one embodiment no more than about 3 hours, in another embodiment no more than about 1.5 hours, and in yet another embodiment no more than about 1 hour, although the time can be outside of these ranges.

Thereafter, the product can be precipitated by addition of a small amount of a non-solvent, such as hexane or methylene chloride, followed by good stirring. The product can then be recovered by filtration.

While not being limited to any particular theory, it is believed that the bis(urea-urethane) compounds disclosed herein form reversible hydrogen bonds, resulting in the formation of oligomers and oligomer networks held together by non-covalent hydrogen bonds instead of covalent bonds. An example of such bond formation is illustrated as follows:

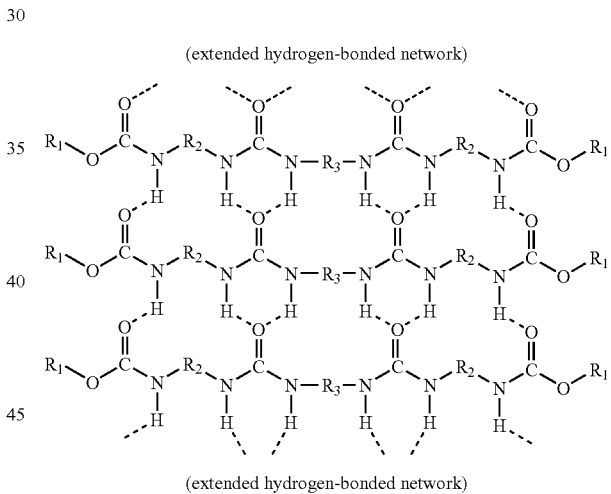

While not being limited to any particular theory, it is believed that in inks containing these bis[urea-urethane] compounds, at least some and perhaps all of these hydrogen bonds can be broken at the temperatures at which hot melt ink jet printing occurs (typically, although not necessarily, over 100° C.). When the ink is printed onto an intermediate transfer member or a final recording substrate, the ink cools as it is printed, which results in reformation of any hydrogen bonds broken by heating. The polymer-like materials thus formed behave like conventional covalently-bonded polymers to enhance image permanence. The image robustness can be increased by adding a bis[urea-urethane] gelator compound to the ink. The gelator molecules can self-assemble into 3-dimensional fibrous networks by intermolecular hydrogen bonding and van der Waals interactions. The molten ink is expected to get trapped into these gel networks and form a semi-solid or a gel.

In addition, the gelled inks exhibit visco-elastic rheological characteristics that are different from those of conventional hot melt or phase change inks in that they show an elastic behavior in a region where the ink is supposed to be in the liquid state. This behavior is evidenced by the crossover of G' (storage modulus) and G" (loss modulus), with G' being higher than G", indicating that the material is elastic. The elasticity of the material can also be expressed using tan-delta, which is defined as the ratio of G" to G', or G"/G'. A material which has a tan-delta of less than one is elastic, whereas a non-elastic material will not have a tan-delta of less than one above its melting point. The bis(urea-urethane) gelator compounds, when present in phase change inks, can enable an intermediate gel phase wherein the gel phase transition entails a tan-delta of in one embodiment less than about 10, in another embodiment less than about 5, and in yet another embodiment less than about 1, although the tan-delta can be outside of these ranges. This elasticity can further enhance the robustness of images generated with the inks containing the bis(urea-urethane) compounds. The bis(urea-urethane) gelator compounds can also enable desirably narrow gel phase transitions in the inks, in one embodiment gel phase transitions 0.1 to 40° C. wide, in another embodiment gel phase transitions 0.1 to 20° C. wide, and in yet another embodiment gel phase transitions 0.1 to 15° C. wide, although the gel phase transitions can be outside of these ranges.

Phase change inks as disclosed herein in one specific embodiment exhibit a gel phase or state from about 1° C. to about 40° C. above the ink melting point, in another specific embodiment exhibit a gel phase or state from about 1° C. to about 20° C. above the ink melting point, and in yet another specific embodiment exhibit a gel phase or state from about 2° C. to about 15° C. above the ink melting point, although the gel phase or state can be exhibited outside of these ranges.

The formation of hydrogen-bonded oligomers or polymers from specific ink carrier materials can be determined by any desired method. For example, a dramatic onset of resinous and viscoelastic characteristics on cooling is indicative of the formation of hydrogen-bonded oligomers or polymers from the ink carrier material or combination of materials. The formation of hydrogen bonds and hydrogen-bonded oligomers or polymers can also be detected by IR spectroscopy. NMR spectroscopy may also help to detect the presence of hydrogen-bonded oligomers or polymers. In situations wherein the ink carrier material is crystalline, X-ray crystallography can be used to define the oligomeric or polymeric structure.

Further information on gels is disclosed in, for example, *Gels Handbook*, Vol. 1-4, Editors-in-Chief, Y. Osada and K. Kajiwara (translated by H. Ishida), 2001, Academic Press, the disclosure of which is totally incorporated herein by reference.

Specific embodiments will now be described in detail. These examples are intended to be illustrative, and the claims are not limited to the materials, conditions, or process parameters set forth in these embodiments. All parts and percentages are by weight unless otherwise indicated.

Example I

Into a solution containing 1,6-diisocyanatohexane (27.7 mmol, 4.66 grams, obtained from Sigma-Aldrich Fine Chemicals, Milwaukee, Wis.) and hexane (250 milliliters) with stirring at room temperature was added a solution of 1-octadecanol (27.7 mmol, 7.5 grams; obtained from Sigma-Aldrich Fine Chemicals) in anhydrous tetrahydrofuran (50 milliliters, from Sigma-Aldrich Fine Chemicals) and dibutyl tin dilaurate (1 mol percent, 0.08 gram, obtained from Sigma-Aldrich Fine Chemicals) as catalyst. The resulting solution was heated to 40° C. for 30 minutes and subsequently cooled to room temperature (20 to 25° C.). A solution of 3,3'-[(1,4-butanediol) bis(propylamine)] (NDPA-12, 2.83 grams, 13.9 mmol, obtained from Tomah Chemical, Milton, Wis.) in hexane (60 milliliters) was slowly added to the reaction mixture through an addition funnel. The mixture was stirred vigorously at room temperature for 30 minutes, during which a more viscous white precipitate was formed. IR spectroscopy indicated the presence of trace amounts of isocyanate. More 3,3'-[(1,4-butanediol) bis(propylamine)] (NDPA-12, 0.4 gram, 2 mol) was added and the mixture was stirred for an additional 30 minutes. IR spectroscopy indicated that all of the isocyanate was consumed. The product was isolated by vacuum filtration on a paper filter, rinsed with hexane, and dried under vacuum at 60° C. for 2 hours to give 14.33 grams of a white powder (93 percent yield). The product was believed to be of the formula

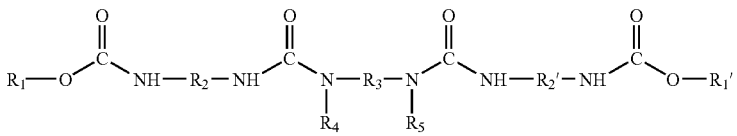

wherein $R_1$ and $R_1'$ were both $-(CH_2)_{17}CH_3$, $R_2$ and $R_2'$ were both $-(CH_2)_6-$, $R_3$ was $-(CH_2)_3-O-(CH_2)_4-O-(CH_2)_3-$, and $R_4$ and $R_5$ were both hydrogen atoms. $^1$H NMR analysis of the product indicated that the product was of high purity. $^1$H NMR (DMSO-$d_6$, at 100° C.); 0.91 ppm (multiplet, 3H integration, C$\underline{H}_3$(CH$_2$)$_{16}$CH$_2$CONH—), 1.02-1.73 ppm (broad multiplet, 44H integration, —CH$_3$(C$\underline{H}_2$)$_{16}$CH$_2$—, NHCONHCH$_2$(C$\underline{H}_2$)$_4$CH$_2$NHCO$_2$—, —CH$_2$C$\underline{H}_2$CH$_2$O—CH$_2$(C$\underline{H}_2$)$_2$CH$_2$—O—CH$_2$C$\underline{H}_2$CH$_2$—), 2.87-3.14 ppm (broad multiplets, 6H integration, —O(CH$_2$)$_2$C$\underline{H}_2$NHCONHC$\underline{H}_2$(CH$_2$)$_4$C$\underline{H}_2$NHCO$_2$), 3.39 ppm (multiplet, 8H, —(CH$_2$)$_2$C$\underline{H}_2$—O—C$\underline{H}_2$(CH$_2$)$_2$C$\underline{H}_2$—O—C$\underline{H}_2$(CH$_2$)$_2$—), 3.96 ppm (triplet, 2H integration, $CH_3(CH_2)_{16}C\underline{H}_2$—OCONH—), 5.53 ppm (broad singlet, 2H integration, —N$\underline{H}$CONH—), 6.49 ppm (broad singlet, 1H integration —N$\underline{H}$CO$_2$).

Example II

Into a solution containing 1,6-diisocyanatohexane (3.50 grams, 20.8 mmol; obtained from Sigma-Aldrich Fine Chemicals) and hexane (250 milliliters) stirring at room temperature was added a solution of 1-octadecanol (5.63 grams, 20.8 mmol; obtained from Sigma-Aldrich Fine Chemicals) in anhydrous tetrahydrofuran (50 milliliters, obtained from Sigma-Aldrich Fine Chemicals) and dibutyl tin dilaurate (0.07 gram, 1 mol %; obtained from Sigma-Aldrich Fine Chemicals) as catalyst. The resulting solution was heated to 60° C. for 1 hour, during which a white precipitate was formed. The mixture was cooled to room temperature (20 to 25° C.). A solution of 1,12-diaminodecane (2.08 grams, 10.4 mmol; obtained from Sigma-Aldrich Fine Chemicals) in hexane (50 milliliters) was then slowly added to the reaction mixture. The mixture was stirred vigorously at room temperature for 1 hour, during which a more viscous white precipitate was formed. IR spectroscopy indicated the presence of trace amounts of isocyanate, which was quenched by adding methanol (5 milliliters). The product was isolated by vacuum filtration on a paper filter, rinsed with hexane, and dried under vacuum at 60° C. for 2 hours to give 8.18 grams of a white powder (73 percent yield). The product was believed to be of the formula

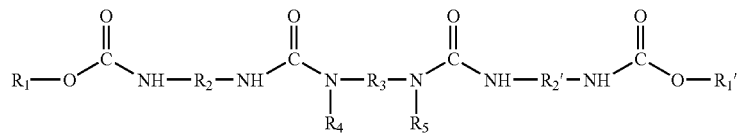

wherein $R_1$ and $R_1'$ were both —$(CH_2)_{17}CH_3$, $R_2$ and $R_2'$ were both —$(CH_2)_6$—, $R_3$ was —$(CH_2)_{12}$—, and $R_4$ and $R_5$ were both hydrogen atoms. The $^1$H NMR of this product was similar to that of Example I.

Example III

Into a solution containing 1,6-diisocyanatohexane (4.33 grams, 25.7 mmol; obtained from Sigma-Aldrich Fine Chemicals) and hexane (250 milliliters) stirring at room temperature was added a solution of 1-docosanol (8.40 grams, 25.7 mmol; obtained from Sigma-Aldrich Fine Chemicals) in anhydrous tetrahydrofuran (50 milliliters, obtained from Sigma-Aldrich Fine Chemicals) and dibutyl tin dilaurate (0.08 gram, 1 mol %; obtained from Sigma-Aldrich Fine Chemicals) as catalyst. The resulting solution was heated to 60° C. for 1 hour, during which a white precipitate was formed. The mixture was cooled to room temperature (20 to 25° C.). A solution of 1,10-diaminodecane (2.21 grams, 12.9 mmol; obtained from Sigma-Aldrich Fine Chemicals) in hexane (50 milliliters) was then slowly added to the reaction mixture through an addition funnel. The mixture was stirred vigorously at room temperature for 1 hour, during which a more viscous white precipitate was formed. All of the isocyanate was consumed as indicated by IR spectroscopy. The product was isolated by vacuum filtration on a paper filter, rinsed with hexane, and dried under vacuum at 60° C. for 2 hours to give 13.8 grams of an off-white powder (93 percent yield). The product was obtained as a white powder in 93 percent yield. The product was believed to be of the formula

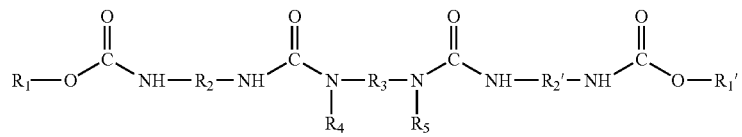

wherein $R_1$ and $R_1'$ were both —$(CH_2)_{21}CH_3$, $R_2$ and $R_2'$ were both —$(CH_2)_6$—, $R_3$ was —$(CH_2)_{10}$—, and $R_4$ and $R_5$ were both hydrogen atoms. The $^1$H NMR of this product was similar to that of Example I.

Example IV

Into a solution containing 4,4'-methylene bis(cyclohexyl isocyanate) (4.2 grams, 16.01 mmol, obtained from Sigma-Aldrich Fine Chemicals) and hexane (250 milliliters) stirring at room temperature was added a solution of isostearyl alcohol (4.33 grams, 16.01 mmol; obtained from UniQema, Wilmington, Del.) in hexane (50 milliliters) and dibutyl tin dilaurate (0.05 grams, 1 mol %, obtained from Sigma-Aldrich Fine Chemicals) as catalyst. The resulting solution was heated to 50° C. for 1 hour, during which the solution turned cloudy. The reaction mixture was cooled to room temperature (20 to 25° C.). A solution of 3,3'-[(1,4-butanediol) bis(propylamine)] (NDPA-12, 1.63 grams, 8.01 mmol, obtained from Tomah Chemical, Milton, Wis.) in hexane (60 milliliters) was slowly added to the reaction mixture through an addition funnel. The mixture was stirred vigorously at room temperature for 1 hour, during which a viscous white precipitate was formed. IR spectroscopy indicated that all of the isocyanate was consumed. The product was isolated by vacuum filtration on a paper filter, rinsed with hexane, and dried under vacuum at 40° C. for 30 minutes to give 7.3 grams of a white powder (72 percent yield). The product was believed to be of the formula

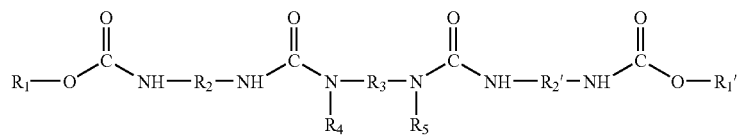

wherein $R_1$ and $R_1'$ were both

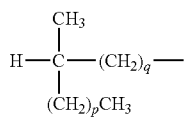

wherein p and q were both integers of from 0 to 15 and the sum of p+q=15, $R_2$ and $R_2'$ were both

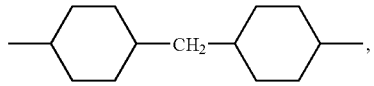

$R_3$ was —$(CH_2)_3$—O—$(CH_2)_4$—O—$(CH_2)_3$, and $R_4$ and $R_5$ were both hydrogen atoms.

Example V

Into a solution containing 1,6-diisocyanatohexane (2.35 grams, 14 mmol; obtained from Sigma-Aldrich Fine Chemicals) and hexane (75 milliliters, obtained from Sigma-Aldrich Fine Chemicals) stirring at room temperature was added 1,4-butanediol vinyl ether (1.62 grams, 14 mmol, obtained from Sigma-Aldrich Fine Chemicals) and dibutyltin dilaurate (0.088 grams, 0.14 mmol, obtained from Sigma-Aldrich Fine Chemicals) as the catalyst. The mixture was stirred and heated to an internal temperature of about 45° C. for 25 minutes. The progress of the reaction was monitored by $^1$H-NMR spectroscopy for consumption of the 1,4-butanediol vinyl ether reactant, indicated by the disappearance of the —$CH_2$OH multiplet, which appears at 3.5 ppm as a shoulder peak on the downfield end of the intermediate isocyanate product whose signal is located at 3.35-3.40 ppm. The mixture was cooled to about 15° C. internal temperature, after which to this mixture was added dropwise a solution of 1,8-diaminooctane (1.2 grams, 8.3 mmol; obtained from Sigma-Aldrich Fine Chemicals) dissolved in anhydrous tetrahydrofuran (10 milliliters). The mixture was stirred for about 60 minutes while warming up to room temperature, and thickened to form a gelatinous slurry. FTIR spectroscopic analysis of a reaction sample showed little unreacted isocyanate (peak at 2180 $cm^{-1}$, sample prepared as a KBr pellet). Any residual isocyanate was quenched by addition of methanol (5 milliliters). The reaction mixture was then filtered by vacuum filtration to give a semi-solid product, which was subsequently stirred in hexane to ensure full precipitation. The solid product was filtered and dried in air to give 4.59 grams of a white powder (92 percent yield). The product was believed to be of the formula

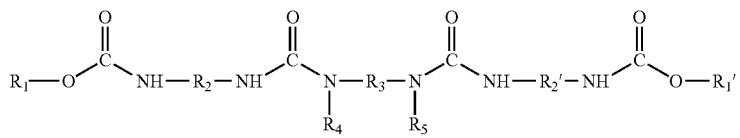

wherein $R_1$ and $R_1'$ were both

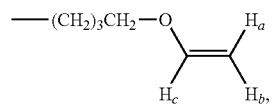

$R_2$ and $R_2'$ were both —$(CH_2)_6$—, $R_3$ was —$(CH_2)_8$—, and $R_4$ and $R_5$ were both hydrogen atoms. $^1$H-NMR spectroscopic analysis of the solid was performed in DMSO-$d_6$ (300 mHz) at high temperature (100° C.) and indicated the above structure with the following assigned peaks: 1.27-1.80 ppm (several multiplets, 34H integration, methylene protons); 2.65 ppm (multiplet, 2H integration, —NH(C=O)NH$\underline{CH_2}$($CH_2)_6$ $\underline{CH_2}$NH(C=O)NH—); 2.95 ppm (multiplet, 8H integration, —O(C=O)NH$\underline{CH_2}$($CH_2)_4$$\underline{CH_2}$NH(C=O)NH—); 3.80 ppm (multiplet, 4H integration, —NH(C=O)OCH$_2$CH$_2$CH$_2$ $\underline{CH_2}$—O—C($\underline{H_c}$)=C($\underline{H_a}$)($\underline{H_b}$)); 4.0 ppm (multiplet, 6H integration, —NH(C=O)OCH$_2$CH$_2$CH$_2$CH$_2$—O—C($\underline{H_c}$)=C( $\underline{H_a}$)($\underline{H_b}$)); 4.25 ppm (doublet, 2H integration, —O—C($\underline{H_c}$)=C ($\underline{H_a}$)($\underline{H_b}$)); 5.50 ppm and 5.70 ppm (broad singlets, each 2H integration, urea NH protons); 6.45 ppm (doublet of doublets, 2H integration, —O—C($\underline{H_c}$)=C($\underline{H_a}$)($\underline{H_b}$)); 6.60 ppm (broad singlet, 2H integration, urethane NH proton). Elemental analysis calculated for C: 60.64%, H, 9.53%, N, 11.78%; found for C, 59.67%, H, 9.11%, N, 12.17%.

Ink Example 1

A cyan ink composition was prepared in a beaker by adding (1) 21.6 grams (61.03 parts by weight) of polyethylene wax (PE 500, obtained from Baker Petrolite, Tulsa, Okla., a polyethylene homopolymer with an average chain length of C-36), (2) 9.76 grams (27.41 parts by weight) of a linear primary long chain alcohol (UNILIN® 425, obtained from Baker Petrolite, Tulsa, Okla., with an average chain length of C-30), (3) 1.27 grams (3.59 parts by weight) of a glycerol ester of hydrogenated (rosin) acid (KE-100, obtained from Arakawa Chemical Industries, Ltd, Osaka, Japan), (4) 0.91 gram (2.57 parts by weight) of an alkylbenzyl phthalate of the formula

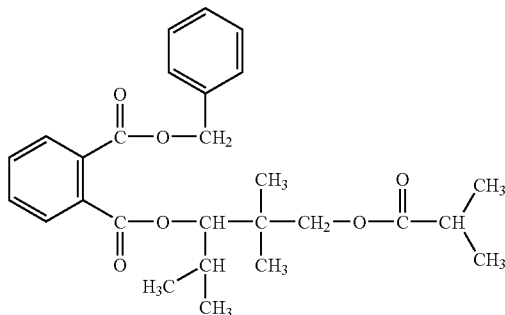

(SANTICIZER® 278, obtained from Ferro Corporation, Bridgeport, N.J.), (5) 0.03 gram (0.08 parts by weight) of NAUGUARD® 445 antioxidant (obtained from Uniroyal Chemical Co., Middlebury, Conn.), and (6) 1.04 grams (2.83 parts by weight) of the bis(urea-urethane) prepared in Example II. The materials were melted together at a temperature of about 135° C. in a reaction block (from H+P Labortechnik GmbH, München) controlled with a telemodel 40CT, and stirred for about 2 hours at about 500 rpm. To this mixture was then added (7) 0.89 gram (2.49 parts by weight) of the cyan colorant disclosed in Example V of U.S. Pat. No. 6,472,523, the disclosure of which is totally incorporated herein by reference. The ink was stirred for about 2 additional hours and then cooled to room temperature. The cyan ink thus prepared exhibited a viscosity of about 13.5 centipoise as measured by an RFS3 Rheometrics parallel-plate viscometer at about 110° C.

Ink Example 2

A cyan ink was prepared as described in Ink Example 1 except that 3.5 parts by weight of the bis(urea-urethane) was added. Relative amounts of the ingredients in this ink, expressed in percent by weight of the ink, is indicated in the table below in Comparative Ink Example A. The cyan ink thus prepared exhibited a viscosity of about 17.6 centipoise as measured by an RFS3 Rheometrics parallel-plate viscometer at about 110° C.

Comparative Ink Example A

A cyan ink was prepared as described in Ink Example 1 except that no bis(urea-urethane) was present. Relative amounts of the ingredients in this ink, expressed in percent by weight of the ink, is indicated in the table below.

| Component | Ink 1 | Ink 2 | Comparative Ink A |
|---|---|---|---|
| PE 500 | 61.20 | 60.60 | 62.81 |
| UNILIN ® 425 | 27.30 | 27.23 | 28.21 |

-continued

| Component | Ink 1 | Ink 2 | Comparative Ink A |
|---|---|---|---|
| KE-100 | 3.58 | 3.57 | 3.69 |
| SANTICIZER ® 278 | 2.56 | 2.55 | 2.65 |
| urea-urethane | 2.81 | 3.50 | 0 |
| NAUGUARD ® 445 | 0.08 | 0.08 | 0.09 |
| cyan colorant | 2.47 | 2.47 | 2.56 |
| Total | 100 | 100 | 100 |

Rheology of the three inks was measured using a controlled strain rheometer, RFS3 from Rheometrics Scientific, in a conventional parallel plate configuration. The table below shows the tan-delta (ratio of loss modulus or viscous modulus, G", to storage modulus or elastic modulus, G') of the two inks in a region above their melting point (melting point of the inks is around 90° C. as determined by the rheometer). Inks 1 and 2 have a lower tan-delta in this region, indicating an increase in G' (elastic modulus). Ink 2, which contained more of the bis(urea-urethane) gelator compound, has a tan delta of less than one at 95° C., indicating that G' is much higher than G", suggesting that the material is elastic in that region. Comparative Ink A, on the other hand, has a high tan-delta in the same region, suggesting a very low elasticity compared to inks 1 and 2. These data demonstrate that the bis(urea-urethane) significantly affects the rheological properties of the solid inks containing it. The increase of elasticity of the ink above its melting point is expected to translate into a more robust image.

| Temperature (° C.) | Ink 1 tan-delta | Ink 2 tan-delta | Ink A tan-delta |
|---|---|---|---|
| 105 | 5.14 | 1.65 | 14 |
| 100 | 3.82 | 1.35 | 17 |
| 95 | 3.66 | 0.76 | 15 |

Ink Example 3

An ink is prepared as described in Ink Example 1 except that the cyan colorant is replaced with 3 parts by weight of the yellow colorant disclosed in Example I of U.S. Pat. No. 6,713,614, the disclosure of which is totally incorporated herein by reference. A yellow phase change ink is thus prepared.

Ink Example 4

An ink is prepared as described in Ink Example 1 except that the bis(urea-urethane) prepared in Example II is replaced by 2.5 parts by weight of the bis(urea-urethane) prepared in Example I.

Ink Example 5

An ink is prepared as described in Ink Example 1 except that the bis(urea-urethane) prepared in Example II is replaced by 2.5 parts by weight of the bis(urea-urethane) prepared in Example III.

Other embodiments and modifications of the present invention may occur to those of ordinary skill in the art subsequent to a review of the information presented herein;

What is claimed is:

1. A bis[urea-urethane] compound of the formula

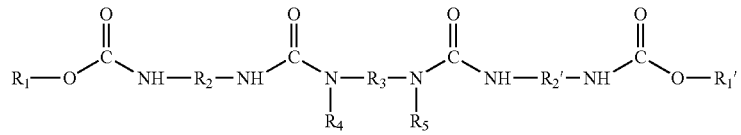

wherein $R_1$ and $R_1'$ each, independently of the other, is an alkyl group selected from the group consisting of (1) linear saturated unsubstituted aliphatic groups containing no hetero atoms, (2) branched saturated unsubstituted aliphatic groups containing no hetero atoms, (3) linear ethylenically unsaturated unsubstituted aliphatic groups containing no hetero atoms, (4) branched ethylenically unsaturated unsubstituted aliphatic groups containing no hetero atoms, (5) linear saturated substituted aliphatic groups containing no hetero atoms, (6) branched saturated substituted aliphatic groups containing no hetero atoms, (7) linear ethylenically unsaturated substituted aliphatic groups containing no hetero atoms, (8) branched ethylenically unsaturated substituted aliphatic groups containing no hetero atoms, (9) linear saturated unsubstituted aliphatic groups containing hetero atoms, (10) branched saturated unsubstituted aliphatic groups containing hetero atoms, (11) linear ethylenically unsaturated unsubstituted aliphatic groups containing hetero atoms, (12) branched ethylenically unsaturated unsubstituted aliphatic groups containing hetero atoms, (13) linear saturated substituted aliphatic groups containing hetero atoms, (14) branched saturated substituted aliphatic groups containing hetero atoms, (15) linear ethylenically unsaturated substituted aliphatic groups containing hetero atoms, (16) branched ethylenically unsaturated substituted aliphatic groups containing hetero atoms wherein at least one of $R_1$ and $R_1'$ has at least about 6 carbon atoms, $R_2$ and $R_2'$ each, independently of the other, is an alkylene group, wherein at least one of $R_2$ and $R_2'$ has at least about 3 carbon atoms, $R_3$ is an alkylene group having at least about 2 carbon atoms, and $R_4$ and $R_5$ each, independently of the other, is a hydrogen atom or an alkyl group, and wherein $R_1$ and $R_1'$ each contain no more than 2 fully fluorinated carbon atoms.

2. A compound according to claim 1 wherein at least one of $R_1$ and $R_1'$ is a linear alkyl group.

3. A compound according to claim 1 wherein at least one of $R_1$ and $R_1'$ is a branched alkyl group.

4. A compound according to claim 1 wherein at least one of $R_1$ and $R_1'$ is a saturated alkyl group.

5. A compound according to claim 1 wherein at least one of $R_1$ and $R_1'$ is an unsaturated alkyl group.

6. A compound according to claim 1 wherein at least one of $R_1$ and $R_1'$ is a substituted alkyl group.

7. A compound according to claim 1 wherein at least one of $R_1$ and $R_1'$ is an unsubstituted alkyl group.

8. A compound according to claim 1 wherein at least one of $R_1$ and $R_1'$ is an alkyl group having hetero atoms therein.

9. A compound according to claim 1 wherein at least one of $R_1$ and $R_1'$ is an alkyl group having no hetero atoms therein.

10. A compound according to claim 1 wherein at least one of $R_1$ and $R_1'$ is an alkyl group having at least about 6 carbon atoms.

11. A compound according to claim 1 wherein at least one of $R_1$ and $R_1'$ is an alkyl group having at least about 10 carbon atoms.

12. A compound according to claim 1 wherein at least one of $R_1$ and $R_1'$ is an alkyl group having at least about 18 carbon atoms.

13. A compound according to claim 1 wherein $R_1$ and $R_1'$ are both alkyl groups having at least about 6 carbon atoms.

14. A compound according to claim 1 wherein $R_1$ and $R_1'$ are both alkyl groups having at least about 10 carbon atoms.

15. A compound according to claim 1 wherein $R_1$ and $R_1'$ are both alkyl groups having at least about 18 carbon atoms.

16. A compound according to claim 1 wherein $R_1$ and $R_1'$ are the same as each other.

17. A compound according to claim 1 wherein $R_1$ and $R_1'$ are different from each other.

18. A compound according to claim 1 wherein at least one of $R_2$ and $R_2'$ is a linear alkylene group.

19. A compound according to claim 1 wherein at least one of $R_2$ and $R_2'$ is a branched alkylene group.

20. A compound according to claim 1 wherein at least one of $R_2$ and $R_2'$ is a saturated alkylene group.

21. A compound according to claim 1 wherein at least one of $R_2$ and $R_2'$ is an unsaturated alkylene group.

22. A compound according to claim 1 wherein at least one of $R_2$ and $R_2'$ is a substituted alkylene group.

23. A compound according to claim 1 wherein at least one of $R_2$ and $R_2'$ is an unsubstituted alkylene group.

24. A compound according to claim 1 wherein at least one of $R_2$ and $R_2'$ is an alkylene group having hetero atoms therein.

25. A compound according to claim 1 wherein at least one of $R_2$ and $R_2'$ is an alkylene group having no hetero atoms therein.

26. A compound according to claim 1 wherein at least one of $R_2$ and $R_2'$ is an alkylene group having at least about 3 carbon atoms.

27. A compound according to claim 1 wherein at least one of $R_2$ and $R_2'$ is an alkylene group having at least about 6 carbon atoms.

28. A compound according to claim 1 wherein $R_2$ and $R_2'$ are both alkylene groups having at least about 3 carbon atoms.

29. A compound according to claim 1 wherein $R_2$ and $R_2'$ are both alkylene groups having at least about 6 carbon atoms.

30. A compound according to claim 1 wherein $R_2$ and $R_2'$ are the same as each other.

31. A compound according to claim 1 wherein $R_2$ and $R_2'$ are different from each other.

32. A compound according to claim 1 wherein $R_3$ is a linear alkylene group.

33. A compound according to claim 1 wherein $R_3$ is a branched alkylene group.

34. A compound according to claim 1 wherein $R_3$ is a saturated alkylene group.

35. A compound according to claim 1 wherein $R_3$ is an unsaturated alkylene group.

36. A compound according to claim 1 wherein $R_3$ is a substituted alkylene group.

37. A compound according to claim 1 wherein $R_3$ is an unsubstituted alkylene group.

38. A compound according to claim 1 wherein $R_3$ is an alkylene group having hetero atoms therein.

39. A compound according to claim 1 wherein $R_3$ is an alkylene group having no hetero atoms therein.

40. A compound according to claim 1 wherein $R_3$ is an alkylene group having at least about 2 carbon atoms.

41. A compound according to claim 1 wherein $R_3$ is an alkylene group having at least about 12 carbon atoms.

42. A compound according to claim 1 wherein $R_3$ is an alkylene group having at least about 36 carbon atoms.

43. A compound according to claim 1 wherein $R_4$ and $R_5$ are each hydrogen atoms.

44. A compound according to claim 1 wherein $R_2$ and $R_2'$ are the same and wherein $R_4$ and $R_5$ are each hydrogen atoms.

45. A compound according to claim 1 wherein $R_2$ and $R_2'$ are the same, $R_1$ and $R_1'$ are the same, and wherein $R_4$ and $R_5$ are each hydrogen atoms.

46. A compound according to claim 1 wherein $R_1$ and $R_1'$ each contain no more than 1 fully fluorinated carbon atom.

47. A compound according to claim 1 wherein $R_1$ and $R_1'$ each contain no fully fluorinated carbon atoms.

48. A compound according to claim 1 wherein $R_1$ and $R_1'$ each contain no fluorine atoms.

49. A compound according to claim 1 wherein $R_1$, $R_1'$, $R_2$, and $R_2'$ contain no fluorine atoms.

50. A compound according to claim 1 wherein $R_1$, $R_1'$, $R_2$, $R_2'$, and $R_3$ contain no fluorine atoms.

51. A compound according to claim 1 wherein $R_1$, $R_1'$, $R_2$, $R_2'$, $R_3$, $R_4$ and $R_5$ contain no fluorine atoms.

52. A compound according to claim 1 wherein $R_1$ and $R_1'$ are both $—(CH_2)_{17}CH_3$, $R_2$ and $R_2'$ are both $—(CH_2)_6—$, $R_3$ is $—(CH_2)_3—O—(CH_2)_4—O—CH_2)_3—$, and $R_4$ and $R_5$ are both hydrogen atoms.

53. A compound according to claim 1 wherein $R_1$ and $R_1'$ are both $—(CH_2)_{17}CH_3$, $R_2$ and $R_2'$ are both $—(CH_2)_6—$, $R_3$ is $—(CH_2)_{12}—$, and $R_4$ and $R_5$ are both hydrogen atoms.

54. A compound according to claim 1 wherein $R_1$ and $R_1'$ are both $—(CH_2)_{21}CH_3$, $R_2$ and $R_2'$ are both $—(CH_2)_6—$, $R_3$ is $—(CH_2)_{10}—$, and $R_4$ and $R_5$ are both hydrogen atoms.

* * * * *